US012692523B2

(12) United States Patent
Hirano et al.

(10) Patent No.: US 12,692,523 B2
(45) Date of Patent: Jul. 28, 2026

(54) METHOD OF PRODUCING L-AMINO ACID

(71) Applicant: Ajinomoto Co., Inc., Tokyo (JP)

(72) Inventors: Seiko Hirano, Kanagawa (JP); Kota Inoue, Kanagawa (JP); Kazuyuki Hayashi, Kanagawa (JP); Kosuke Yokota, Kanagawa (JP); Mika Moriya, Kanagawa (JP); Tomoko Suzuki, Kanagawa (JP); Yoshitomo Kadokura, Kanagawa (JP); Takeshi Nagahiko, Mie (JP); Akari Tashiro, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 527 days.

(21) Appl. No.: 18/307,947

(22) Filed: Apr. 27, 2023

(65) Prior Publication Data

US 2023/0416793 A1 Dec. 28, 2023

Related U.S. Application Data

(63) Continuation of application No. PCT/JP2021/039281, filed on Oct. 25, 2021.

(30) Foreign Application Priority Data

Oct. 28, 2020 (JP) ................................. 2020-180304

(51) Int. Cl.
| | |
|---|---|
| *C12P 13/14* | (2006.01) |
| *C12N 9/02* | (2006.01) |
| *C12N 9/04* | (2006.01) |
| *C12N 9/10* | (2006.01) |
| *C12N 9/12* | (2006.01) |
| *C12N 9/16* | (2006.01) |
| *C12N 9/88* | (2006.01) |
| *C12N 15/77* | (2006.01) |
| *C12R 1/15* | (2006.01) |

(52) U.S. Cl.
CPC ............ *C12P 13/14* (2013.01); *C12N 9/0006* (2013.01); *C12N 9/0008* (2013.01); *C12N 9/1096* (2013.01); *C12N 9/1217* (2013.01); *C12N 9/16* (2013.01); *C12N 9/88* (2013.01); *C12N 15/77* (2013.01); *C12R 2001/15* (2021.05); *C12Y 101/0104* (2013.01); *C12Y 102/04001* (2013.01); *C12Y 206/01001* (2013.01); *C12Y 207/02001* (2013.01); *C12Y 301/03011* (2013.01); *C12Y 401/02009* (2013.01)

(58) Field of Classification Search
None
See application file for complete search history.

(56) References Cited

U.S. PATENT DOCUMENTS

| | | | |
|---|---|---|---|
| 2008/0032374 A1 | 2/2008 | Zelder et al. | |
| 2010/0099152 A1 | 4/2010 | Chinen et al. | |
| 2012/0237985 A1* | 9/2012 | Nagahiko ............... | C12P 13/14 |
| | | | 435/114 |
| 2013/0260425 A1 | 10/2013 | Doi et al. | |
| 2013/0288325 A1 | 10/2013 | Liao et al. | |
| 2016/0068831 A1* | 3/2016 | Beck ...................... | C12Q 1/527 |
| | | | 435/252.32 |
| 2016/0222394 A1* | 8/2016 | Yamada ................... | C12N 9/88 |
| 2018/0094285 A1 | 4/2018 | Moriya et al. | |
| 2018/0208909 A1 | 7/2018 | Park et al. | |
| 2020/0190486 A1* | 6/2020 | Park ...................... | C12N 9/1217 |
| 2020/0283811 A1* | 9/2020 | Koch ........................ | C12P 7/18 |

FOREIGN PATENT DOCUMENTS

| | | |
|---|---|---|
| CN | 101374953 A | 2/2009 |
| CN | 107893089 A | 4/2018 |
| JP | 2008-509661 A | 4/2008 |
| JP | 2013-544516 A | 12/2013 |
| JP | 2014-036576 A | 2/2014 |
| JP | 2016-163540 A | 9/2016 |
| JP | 2018-520687 A | 8/2018 |
| TW | 200533745 A | 10/2005 |
| WO | WO2006/016705 A1 | 2/2006 |
| WO | WO2019/166647 A1 | 9/2019 |

OTHER PUBLICATIONS

Chinen et al., Innovative Metabolic Pathway Design for Efficient L-Glutamate Production by Suppressing CO2 Emission, J. Biosci. Bioeng. 103, 2007, 262-69. (Year: 2007).*
Uniprot, Accession No. P0A9C9, 2019, www.uniprot.org. (Year: 2019).*
Hernard et al., Phosphoketolase pathway engineering for carbon-efficient biocatalysis, Curr. Opinion Biotechnol. 36, 2015, 183-88. (Year: 2015).*
Lee et al., Hybrid Embden-Meyerhof-Parnas Pathway for Reducing CO2 Loss and Increasing the Acetyl-CoA Levels during Microbial Fermentation, ACS Sustainable Chem. Eng. 9, Sep. 2021, 12394-12405. (Year: 2021).*
Uniprot, Accession No. P77845, 2019, www.uniprot.org. (Year: 2019).*

(Continued)

*Primary Examiner* — Todd M Epstein
(74) *Attorney, Agent, or Firm* — Cermak & McGowan LLP; Shelly Guest Cermak

(57) ABSTRACT

Provided is a method of producing an L-amino acid such as L-glutamic acid and the like. An L-amino-acid is produced by cultivating a coryneform bacterium having L-amino acid-producing ability in a culture medium, which has been modified so as to have one or more of the following modifications: (A) a modification for increasing activity of acetate kinase, (B) a modification for increasing activity of fructose-1,6-bisphosphatase, (C) a modification for decreasing activity of pyruvate dehydrogenase, (D) a modification for decreasing activity of aspartate transaminase, and (E) a modification for decreasing activity of malic enzyme; and collecting the L-amino acid from the culture medium and/or the bacterial cells.

6 Claims, 4 Drawing Sheets

Specification includes a Sequence Listing.

(56)                    References Cited

OTHER PUBLICATIONS

Partial supplementary European search report dated May 19, 2025 issued in corresponding EP application No. 21886136.7.

Chinen A., et al., "Innovative Metabolic Pathway Design for Efficient L-Glutamate Production by Suppressing CO2 Emission," Journal of Bioscience and Bioengineering, vol. 103, No. 3, Mar. 1, 2007, pp. 262-269, XP022028172.

Reinscheid, D. R., et al., "Cloning, sequence analysis, expression and inactivation of the Corynebacterium glutamicum pta-ack operon encoding phosphotransacetylase and acetate kinase," Microbiology, vol. 145, No. 2, Feb. 1, 1999, pp. 503-513, XP093274659.

Nakamura, J. et al., "Mutations of the Corynebacterium glutamicum NCgl1221 Gene, Encoding a Mechanosensitive Channel Homolog, Induce L-Glutamic Acid Production," Applied and Environmental Microbiology, vol. 73, No. 14, Jul. 1, 2007, pp. 4491-4498, XP002691368.

Spector, M. P., "Metabolism, Central (Intermediary)" In: "Encyclopedia of Microbiology (Third Edition)", Feb. 17, 2009, pp. 242-264, XP093274630, Retrieved from the Internet: URL:https://www.sciencedirect.com/science/article/abs/pii/B978012373944500078X?via%3Dihub on May 27, 2025.

Zahoor, A., et al., "Metabolic Engineering of Corynebacterium Glutamicum Aimed at Alternative Carbon Sources and New Products," Computational and Structural Biotechnology Journal, vol. 3, No. 4, Oct. 1, 2012, pp. 1-11, XP055203417.

Huergo, L. F., et al., "The Emergence of 2-Oxoglutarate as a Master Regulator Metabolite," Microbiology and Molecular Biology Reviews, vol. 79, No. 4, Dec. 1, 2015, pp. 419-435, XP093274750.

Yang, H., et al., "Systems metabolic engineering of Bacillus subtilis for efficient biosynthesis of 5-methyltetrahydrofolate," Biotechnol. Bioeng. 2020; 117:2116-2130.

Kikuchi, M., et al., "Glutamic Acid," biotechnology of amino acid production, Ed. Aida, K., et al., Tokyo, Kodansha Ltd. 1986, pp. 101-116 (corresponding to Kunihiko Akashi et al. Amino Acid Fermentation, Academic Press Center, pp. 195-215, 1986).

International Search Report for International App. No. PCT/JP2021/039281 (Nov. 22, 2021).

* cited by examiner

METHOD OF PRODUCING L-AMINO ACID

This application is a Continuation of, and claims priority under 35 U.S.C. § 120 to, International Application No. PCT/JP2021/039281, filed Oct. 25, 2021, and claims priority therethrough under 35 U.S.C. § 119 to Japanese Patent Application No. 2020-180304, filed Oct. 28, 2020, the entireties of which, as well as all citations cited herein, are incorporated by reference herein. The Sequence Listing filed herewith in ST.26.xml format named 2023-04-26T_US-649_SEQ_LIST.xml, 42,398 bytes, generated on Apr. 26, 2023 is also incorporated by reference.

BACKGROUND

Technical Field

The present invention relates to a method of producing an L-amino acid such as L-glutamic acid by fermentation using a bacterium. L-amino acids are industrially useful as raw materials in seasonings and the like.

Background Art

L-amino acids are industrially produced, for example, by fermentation using microorganisms such as bacteria capable of producing an L-amino acid (see Kunihiko Akashi et al. Amino Acid Fermentation, Academic Press Center, pp. 195-215, 1986). As such microorganisms, for example, strains isolated from nature and their mutant strains are used. Moreover, the ability to produce L-amino acids from microorganisms can be improved by using recombinant DNA techniques.

SUMMARY

An aspect of the present invention is the development of a novel technique for improving an ability of a bacterium to produce an L-amino acid and to provide a method of efficiently producing an L-amino acid.

The ability of a coryneform bacterium to produce an L-amino acid can be improved by modifying the bacterium so as to have one or more of the following modifications:

(A) a modification for increasing activity of acetate kinase;

(B) a modification for increasing activity of fructose-1,6-bisphosphatase;

(C) a modification for decreasing activity of pyruvate dehydrogenase;

(D) a modification for decreasing activity of aspartate transaminase; and (E) a modification for decreasing activity of malic enzyme.

An aspect of the present invention is to provide a method of producing an L-amino acid, comprising cultivating a coryneform bacterium having an L-amino acid-producing ability in a culture medium to accumulate an L-amino acid in the culture medium and/or in cells of the bacterium; and collecting the L-amino acid from the culture medium and/or the cells, wherein the L-amino acid is of glutamic acid family, and wherein the bacterium has the following modifications: (X) a modification for increasing availability of a carbon source via phosphoketolase pathway; and/or (Y) a modification for increasing intracellular oxaloacetic acid pool.

It is a further aspect of the present invention to provide the method as described above, wherein the bacterium has at least the modification (X).

It is a further aspect of the present invention to provide the method as described above, wherein the modification (X) is selected from the group consisting of: (A) a modification for increasing activity of acetate kinase, (B) a modification for increasing activity of fructose-1,6-bisphosphatase, (C) a modification for decreasing activity of pyruvate dehydrogenase, and (D) combinations thereof; and wherein the modification (Y) is selected from the group consisting of: (E) a modification for decreasing activity of aspartate transaminase, (F) a modification for decreasing activity of malic enzyme, and (G) combinations thereof.

It is a further aspect of the present invention to provide a method of producing an L-amino acid, comprising: cultivating a coryneform bacterium having L-amino acid-producing ability in a culture medium to accumulate an L-amino acid in the culture medium and/or in cells of the bacterium; and collecting the L-amino acid from the culture medium and/or the cells, wherein the L-amino acid is of glutamic acid family, and wherein the bacterium has a modification selected from the group consisting of: (A) a modification for increasing activity of acetate kinase, (B) a modification for increasing activity of fructose-1,6-bisphosphatase, (C) a modification for decreasing activity of pyruvate dehydrogenase, (D) a modification for decreasing activity of aspartate transaminase, (E) a modification for decreasing activity of malic enzyme, and (F) combinations thereof.

It is a further aspect of the present invention to provide the method as described above, wherein the bacterium has at least the modification (A).

It is a further aspect of the present invention to provide the method as described above, wherein the aspartate transaminase is encoded by aspT gene, wherein the malic enzyme is encoded by malE gene, wherein the pyruvate dehydrogenase is encoded by poxB gene, wherein the acetate kinase is encoded by ack gene, and wherein the fructose-1,6-bisphosphatase is encoded by glpX gene.

It is a further aspect of the present invention to provide the method as described above, wherein the activity of the aspartate transaminase is reduced by decreasing expression of or disrupting a gene encoding aspartate transaminase, wherein the activity of the malic enzyme is reduced by decreasing expression of or disrupting a gene encoding malic enzyme, wherein the activity of the pyruvate dehydrogenase is reduced by decreasing expression of or disrupting a gene encoding pyruvate dehydrogenase, wherein the activity of the acetate kinase is increased by increasing expression of a gene encoding acetate kinase, and wherein the activity of the fructose-1,6-bisphosphatase is increased by increasing expression of a gene encoding fructose-1,6-bisphosphatase It is a further aspect of the present invention to provide the method as described above, wherein expression of the gene encoding acetate kinase is increased by increasing the copy number of the gene and/or by modifying an expression regulatory sequence of the gene, and/or wherein expression of the gene encoding fructose-1,6-bisphosphatase is increased by increasing the copy number of the gene and/or by modifying an expression regulatory sequence of the gene.

It is a further aspect of the present invention to provide the method as described above, wherein the aspartate transaminase is selected from the group consisting of: (1a) a protein comprising the amino acid sequence of SEQ ID NO: 2, (1b) a protein comprising the amino acid sequence of SEQ ID NO: 2 except that said amino acid sequence includes substitution, deletion, insertion, and/or addition of 1 to 10 amino acid residues and has aspartate transaminase activity, and (1c) a protein comprising an amino acid sequence having 90% or more identity to the amino acid sequence of SEQ ID NO: 2 and has aspartate transaminase activity; wherein the malic enzyme is selected from the group consisting of: (2a) a protein comprising the amino acid sequence of SEQ ID NO: 4, (2b) a protein comprising the amino acid sequence of SEQ ID NO: 4 except that said amino acid sequence includes substitution, deletion, insertion, and/or addition of 1 to 10 amino acid residues and has malic enzyme activity, and (2c) a protein comprising an amino acid sequence having 90% or more identity to the amino acid sequence of SEQ ID NO: 4 and has malic enzyme activity; wherein the pyruvate dehydrogenase is selected from the group consisting of: (3a) a protein comprising the amino acid sequence of SEQ ID NO: 6, (3b) a protein comprising the amino acid sequence of SEQ ID NO: 6 except that said amino acid sequence includes substitution, deletion, insertion, and/or addition of 1 to 10 amino acid residues and has pyruvate dehydrogenase activity, and (3c) a protein comprising an amino acid sequence having 90% or more identity to the amino acid sequence of SEQ ID NO: 6 and has pyruvate dehydrogenase activity; wherein the acetate kinase is selected from the group consisting of: (4a) a protein comprising the amino acid sequence of SEQ ID NO: 8 or 10, (4b) a protein comprising the amino acid sequence of SEQ ID NO: 8 or 10 except that said amino acid sequence includes substitution, deletion, insertion, and/or addition of 1 to 10 amino acid residues and has acetate kinase activity, and (4c) a protein comprising an amino acid sequence having 90% or more identity to the amino acid sequence of SEQ ID NO: 8 or 10 and has acetate kinase activity; and/or wherein the fructose-1,6-bisphosphatase is selected from the group consisting of: (5a) a protein comprising the amino acid sequence of SEQ ID NO: 12 or 14, (5b) a protein comprising the amino acid sequence of SEQ ID NO: 12 or 14 except that said amino acid sequence includes substitution, deletion, insertion, and/or addition of 1 to 10 amino acid residues and has fructose-1,6-bisphosphatase activity, and (5c) a protein comprising an amino acid sequence having 90% or more identity to the amino acid sequence of SEQ ID NO: 12 or 14 and has fructose-1,6-bisphosphatase activity.

It is a further aspect of the present invention to provide the method as described above, wherein the bacterium has been further modified so that the activity of phosphoketolase is increased as compared to an unmodified bacterium.

It is a further aspect of the present invention to provide the method as described above, wherein the phosphoketolase is D-xylulose-5-phosphate phosphoketolase and/or fructose 6-phosphate phosphoketolase.

It is a further aspect of the present invention to provide the method as described above, wherein the bacterium is a bacterium of the genus *Corynebacterium.*

It is a further aspect of the present invention to provide the method as described above, wherein the bacterium is *Corynebacterium glutamicum.*

It is a further aspect of the present invention to provide the method as described above, wherein the L-amino acid of glutamic acid family is selected from the group consisting of L-glutamic acid, L-glutamine, L-proline, L-arginine, L-citrulline, L-ornithine, and combinations thereof.

It is a further aspect of the present invention to provide the method as described above, wherein the L-amino acid of glutamic acid family is L-glutamic acid.

It is a further aspect of the present invention to provide the method as described above, wherein the L-glutamic acid is ammonium L-glutamate or sodium L-glutamate.

DETAILED DESCRIPTION OF EXEMPLARY EMBODIMENTS

Figure 1:
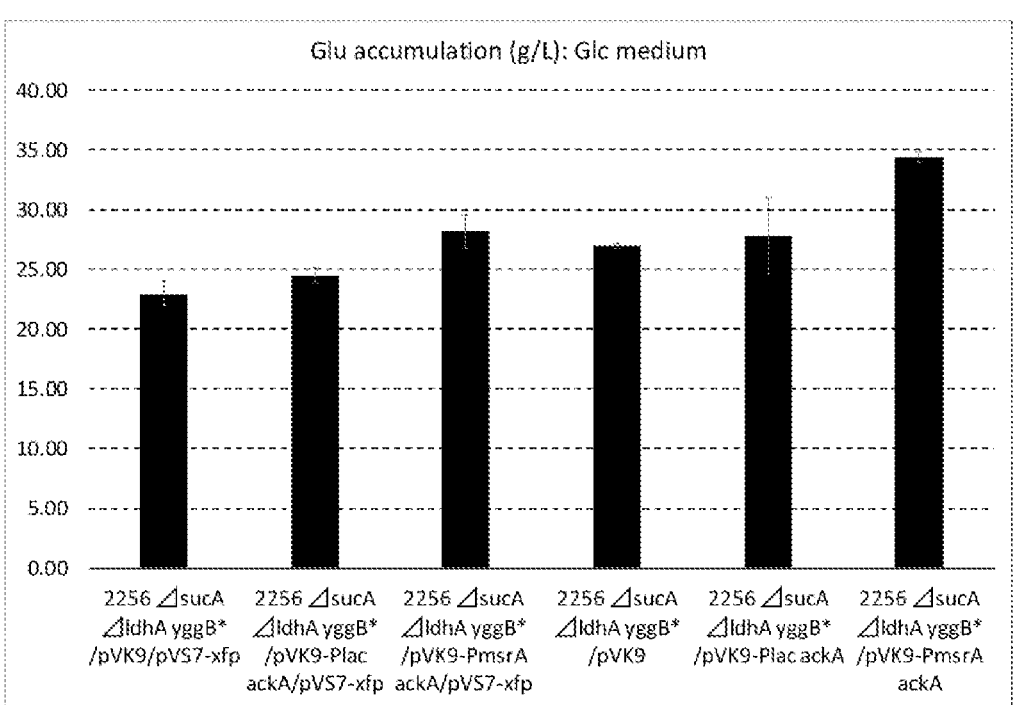
FIG. 1 shows the amount of L-glutamic acid accumulated in a control strain and a strain with enhanced expression of ack gene when glucose is used as a carbon source.

Described herein is a method of producing an L-amino acid by cultivating a coryneform bacterium having L-amino acid-producing ability in a culture medium and accumulating an L-amino acid in the culture medium and/or in bacterial cells; and collecting the L-amino acid from the culture medium and/or the bacterial cells; and also described herein is a method wherein the bacterium is modified so to have specific properties. The bacterium used in the method is also referred to as the "bacterium."

<1> Bacterium

The bacterium is a coryneform bacterium having an L-amino acid-producing ability, modified so that it has specific properties.

<1-1> Bacterium Having L-Amino Acid-Producing Ability

The expression "bacterium having an L-amino acid-producing ability" refers to a bacterium having an ability to produce a target L-amino acid when cultured in a culture medium, and to accumulate it in the culture medium and/or bacterial cells to the extent that it can be collected. The bacterium having the L-amino acid-producing ability may be a bacterium capable of accumulating a target L-amino acid in a culture medium and/or bacterial cells in greater amounts than an unmodified strain. The term "unmodified strain" refers to a control strain that has not been modified so as to have specific properties. In other words, the unmodified strains include a wild-type strain and a parent strain. Moreover, the bacterium having the L-amino acid-producing ability may also be a bacterium capable of accumulating a target L-amino acid in a culture medium in an amount of 0.5 g/L or more, or in an amount of 1.0 g/L or more.

The L-amino acid produced is an L-amino acid of glutamic acid family. The "L-amino acid of glutamic acid family" is a generic term for L-glutamic acid and L-amino acids that are biosynthesized using L-glutamic acid as an intermediate. L-amino acids biosynthesized using L-glutamic acid as an intermediate include L-glutamine, L-proline, L-arginine, L-citrulline, and L-ornithine. The L-amino acids of glutamic acid family particularly include L-glutamic acid. The bacterium may have a single type of L-amino acid-producing ability, or two or more types of L-amino acid-producing ability.

The term "amino acid" refers to an L-amino acid unless otherwise specified. Moreover, the term "L-amino acid" refers to a free L-amino acid, salts thereof, or mixtures thereof, unless otherwise specified, in the present invention. The salts will be described below.

Coryneform bacteria include bacteria belonging to genera such as *Corynebacterium, Brevibacterium*, and *Microbacterium*.

Coryneform bacteria specifically include the following species:

*Corynebacterium acetoacidophilum,*
*Corynebacterium acetoglutamicum,*
*Corynebacterium* alkanolyticum,
*Corynebacterium callunae,*
*Corynebacterium crenatum,*
*Corynebacterium glutamicum,*
*Corynebacterium lilium,*
*Corynebacterium melassecola,*
*Corynebacterium thermoaminogenes (Corynebacterium efficiens,*
*Corynebacterium herculis,*
*Brevibacterium divaricatum (Corynebacterium glutamicum),*
*Brevibacterium flavum (Corynebacterium glutamicum),*
*Brevibacterium* immariophilum,
*Brevibacterium lactofermentum (Corynebacterium glutamicum),*
*Brevibacterium roseum,*
*Brevibacterium saccharolyticum,*
*Brevibacterium* thiogenitalis,
*Corynebacterium* arnrnoniagenes *(Corynebacterium stationis),*
*Brevibacterium* album,
*Brevibacterium* cerinum, and
*Microbacterium* ammoniaphilum.

Coryneform bacteria particularly include *Corynebacterium glutamicum* (formerly known as *Brevibacterium lactofermentum*).

Specific examples of coryneform bacteria include the following strains:

*Corynebacterium acetoacidophilum* ATCC 13870,
*Corynebacterium acetoglutamicum* ATCC 15806,
*Corynebacterium* alkanolyticum ATCC 21511,
*Corynebacterium callunae* ATCC 15991,
*Corynebacterium crenatum* AS1.542,
*Corynebacterium glutamicum* ATCC 13020, ATCC 13032, ATCC 13060, ATCC 13869, FERM BP-734,
*Corynebacterium lilium* ATCC 15990,
*Corynebacterium melassecola* ATCC 17965,
*Corynebacterium efficiens (Corynebacterium thermoaminogenes)* AJ12340 (FERM BP-1539),
*Corynebacterium herculis* ATCC 13868,
*Brevibacterium divaricatum (Corynebacterium glutamicum)* ATCC 14020,
*Brevibacterium flavum (Corynebacterium glutamicum)* ATCC 13826, ATCC 14067, AJ12418 (FERM BP-2205),
*Brevibacterium* immariophilum ATCC 14068,
*Brevibacterium lactofermentum (Corynebacterium glutamicum)* ATCC 13869,
*Brevibacterium roseum* ATCC 13825,
*Brevibacterium saccharolyticum* ATCC 14066,
*Brevibacterium* thiogenitalis ATCC 19240,
*Corynebacterium ammoniagenes (Corynebacterium stationis)* ATCC 6871, ATCC 6872
*Brevibacterium* album ATCC 15111,
*Brevibacterium* cerinum ATCC 15112, and
*Microbacterium* ammoniaphilum ATCC 15354.

Ccoryneform bacteria further particularly include *Brevibacterium lactofermentum* (new name: *Corynebacterium glutamicum*) ATCC 13869.

Note, however, *Corynebacterium* bacteria also include bacteria that had previously been classified into the genus *Brevibacterium*, however, but are now currently united into the genus *Corynebacterium* (Int. J. Syst. Bacteriol., 41, 255 (1991)). Moreover, *Corynebacterium stationis* include bacteria that had previously been classified as *Corynebacterium ammoniagenes*, but are now re-classified into *Corynebacterium stationis* on the basis of nucleotide sequence analysis of 16S rRNA and the like (Int. J. Syst. Evol. Microbiol., 60, 874-879 (2010)).

These strains are available from, for example, the American Type Culture Collection (Address: P. O. Box 1549, Manassas, VA 20108, United States of America). That is, registration numbers are given to the respective strains, and the strains can be ordered using these registration numbers (refer to http://www.atcc.org/). The registration numbers of the strains are listed in the catalogue of the American Type Culture Collection. These strains can also be obtained from, for example, the depositories where the strains were deposited.

The bacterium may inherently have the L-amino acid-producing ability, or may be modified so as to have the L-amino acid-producing ability. The bacterium having the L-amino acid-producing ability, can be obtained by imparting the L-amino acid-producing ability to such a bacterium as described above, or by enhancing the L-amino acid-producing ability of such a bacterium as described above.

The L-amino acid-producing ability can be imparted or enhanced by a method conventionally adopted in the breeding of amino acid producing-bacteria such as coryneform bacteria or *Escherichia* bacteria (see, "Amino Acid Fermentation," Gakkai Shuppan Center (Ltd.), 1st Edition, published May 30, 1986, PP. 77-100). Examples of such methods include, acquiring an auxotrophic mutant strain, acquiring an L-amino acid analogue-resistant strain, acquiring a metabolic regulation mutant strains, and constructing a recombinant strain in which the activity of an L-amino acid biosynthetic enzyme is enhanced. In the breeding of bacteria able to produce an L-amino acid, one of the aforementioned properties, such as auxotrophy, analogue resistance, metabolic regulation mutation may be imparted singly, or two or three or more of such properties may be imparted in combination. Furthermore, in the breeding of bacteria able to produce an L-amino acid, the activity of one of L-amino acid biosynthetic enzymes may be enhanced singly, or the activities of two or three or more of such enzymes may be enhanced in combination. Furthermore, imparting of properties such as auxotrophy, analogue resistance, and metabolic regulation mutation may be combined with enhancing the activity of biosynthetic enzymes.

An auxotrophic mutant strain, analog resistant strain, or metabolic regulation mutant strain, having L-amino acid-producing ability can be obtained by subjecting a parent strain or the wild-type strain to a known mutagenesis treatment, and then selecting a strain exhibiting autotrophy, analogue resistance, or a metabolic regulation mutation and having the L-amino acid-producing ability from the resulting mutant strains. Examples of the known mutagenesis treatment can include X-ray or ultraviolet irradiation, and a treatment with a mutation agent such as N-methyl-N'-nitro-N-nitrosoguanidine (MNNG), and ethyl methane sulfonate (EMS), methyl methane sulfonate (MMS).

The L-amino acid-producing ability can also be imparted or enhanced by enhancing the activity of an enzyme involved in biosynthesis of a target L-amino acid. An enzyme activity can be enhanced by, for example, modifying a bacterium so as to enhance expression of a gene encoding the enzyme. Methods of enhancing gene expression are described in WO 00/18935, EP1010755A, and the like. The detailed procedures for enhancing enzyme activity will be described below.

Furthermore, the L-amino acid-producing ability can be imparted or enhanced by reducing the activity of an enzyme that catalyzes a reaction branching away from the biosynthetic pathway of a target L-amino acid so that a compound other than the target L-amino acid is produced. Note, however, the "enzyme that catalyzes a reaction branching away from the biosynthetic pathway of a target L-amino acid so that a compound other than the target L-amino acid is produced" includes an enzyme involved in the decomposition of the target amino acid. The method of reducing the enzyme activity will be described below.

Hereinafter, bacteria able to produce an L-amino acid and methods of imparting or enhancing L-amino acid-producing ability are specifically exemplified. It is noted that all of the properties of bacteria able to produce an L-amino acid as exemplified below and modifications imparting or enhancing L-amino acid-producing ability may be used singly or in any appropriate combination.

<L-Glutamic-Acid Producing-Bacteria>

Examples of methods of imparting or enhancing an ability to produce an L-glutamic acid can include a method of modifying a bacterium so that the bacterium has an increased activity or activities of one or more types of enzymes such as L-glutamic acid biosynthesis enzymes. Such enzymes include but are not particularly limited to, glutamate dehydrogenase (gdhA), glutamine synthetase (glnA), glutamate synthase (gltBD), isocitrate dehydrogenase (icdA), aconitate hydratase (acnA, acnB), citrate synthase (gltA), methyl citrate synthase (prpC), pyruvate carboxylase (pyc), pyruvate dehydrogenase (aceEF, 1pdA), pyruvate kinase (pykA, pykF), phosphoenolpyruvate synthase (ppsA), enolase (eno), phosphoglyceromutase (pgmA, pgml), phosphoglycerate kinase (pgk), glyceraldehyde-3-phosphate dehydrogenase (gapA), triose phosphate isomerase (tpiA), fructose bisphosphate aldolase (fbp), glucose phosphate isomerase (pgi), 6-phosphogluconate dehydratase (edd), 2-keto-3-deoxy-6-phosphogluconate aldolase (eda), and transhydrogenase (pntAB). Shown in the parentheses after each enzyme is the name of the corresponding gene encoding the enzyme (the same shall apply for the following description). An activity or activities of one or more of, for example, glutamate dehydrogenase, citrate synthase, phosphoenol pyruvate carboxylase, and methyl citrate synthase can be enhanced.

Coryneform bacteria modified so as to increase expression of the glutamate synthase gene (gltBD) include those disclosed in WO 99/07853.

Examples of methods of imparting or enhancing L-glutamic acid-producing ability also include a method of modifying a bacterium so that the bacterium has a reduced activity or activities of one or more types of enzymes that catalyze a reaction branching away from the biosynthetic pathway of L-glutamic acid to generate a compound other than L-glutamic acid. Examples of such enzymes include, but are not particularly limited to, isocitrate lyase (aceA), α-ketoglutarate dehydrogenase (sucA, odhA), acetolactate synthase (ilvI), formate acetyltransferase (pfl), lactate dehydrogenase (ldh), alcohol dehydrogenase (adh), glutamate decarboxylase (gadAB), and succinate dehydrogenase (sdhABCD). For example, among these enzymes, the activity of α-ketoglutarate dehydrogenase can be reduced or deleted.

Coryneform bacteria with a reduced or deficient α-ketoglutarate dehydrogenase activity and methods of acquiring such bacteria are described in WO 2008/075483. Specific examples of coryneform bacteria with a reduced or deficient α-ketoglutarate dehydrogenase activity include the following strains

*Corynebacterium glutamicum* (*Brevibacterium lactofermentum*) L30-2 strain (Japanese Patent Laid-Open (Kokai) No. 2006-340603)

*Corynebacterium glutamicum* (*Brevibacterium lactofermentum*) AS strain (WO

*Corynebacterium glutamicum* (*Brevibacterium lactofermentum*) AJ12821 (FERM BP-4172; French Patent No. 9401748)

*Corynebacterium glutamicum* (*Brevibacterium flavum*) AJ12822 (FERM BP-4173; French Patent No. 9401748)

*Corynebacterium glutamicum* AJ12823 (FERM BP-4174; French Patent No. 9401748)

Examples of L-glutamic acid-producing bacteria and parental strains from which they can be derived also include strains in which both the α-ketoglutarate dehydrogenase (sucA) activity and the succinate dehydrogenase (sdh) activity are reduced or deleted (Japanese Patent Laid-open (Kokai) No. 2010-041920). Specific examples of such strains include an odhAsdhA double-deleted strain of *Corynebacterium glutamicum* ATCC14067 (*Corynebacterium glutamicum* 8L3GΔSDH strain) (Japanese Patent Laid-Open (Kokai) No. 2010-041920).

Moreover, examples of methods of imparting or enhancing the L-glutamic acid-producing ability also can include a method of enhancing the expression of an L-glutamic acid secretion genes such as yhfK gene (WO 2005/085419) and ybjL gene (WO 2008/133161).

Furthermore, examples of methods of imparting or enhancing the L-glutamic acid-producing ability to or in coryneform bacteria also include methods of imparting resistance to an organic acid analogue, respiratory inhibitor, or the like, and methods of imparting sensitivity to a cell wall synthesis inhibitor. Specific examples of such methods include the method of imparting monofluoroacetic acid resistance (Japanese Patent Laid-Open (Kokai) No. 50-113209), the method of imparting adenine resistance or thymine resistance (Japanese Patent Laid-Open (Kokai) No. 57-065198), the method of attenuating urease (Japanese Patent Laid-Open (Kokai) No. 52-038088), the method of imparting malonic acid resistance (Japanese Patent Laid-Open (Kokai) No. 52-038088), the method of imparting resistance to benzopyrones or naphthoquinones (Japanese Patent Laid-open (Kokai) No. 56-1889), the method of imparting HOQNO resistance (Japanese Patent Laid-open (Kokai) No. 56-140895), the method of imparting α-ketomalonic acid resistance (Japanese Patent Laid-Open (Kokai) No. 57-2689), the method of imparting guanidine resistance (Japanese Patent Laid-Open (Kokai) No. 56-35981), and the method of imparting sensitivity to penicillin (Japanese Patent Laid-Open (Kokai) No. 4-88994).

Specific examples of such resistant or susceptible bacteria include the following strains:

*Corynebacterium glutamicum* (*Brevibacterium flavum*) AJ 3949 (FERM BP-2632; Japanese Patent Laid-Open (Kokai) No. 50-113209)

*Corynebacterium glutamicum* AJ11628 (FERM P-5736; Japanese Patent Laid-Open (Kokai) No. 57-065198)

*Corynebacterium glutamicum* (*Brevibacterium flavum*) AJ 11355 (FERM P-5007; Japanese Patent Laid-Open (Kokai) No. 56-1889)

*Corynebacterium glutamicum* AJ 11368 (FERM P-5020; Japanese Patent Laid-Open (Kokai) No. 56-1889)

*Corynebacterium glutamicum* (*Brevibacterium flavum*) AJ11217 (FERM P-4318; Japanese Patent Laid-Open (Kokai) No. 57-2689)

*Corynebacterium glutamicum* AJ 11218 (FERM P-4319; Japanese Patent Laid-Open (Kokai) No. 57-2689)

*Corynebacterium glutamicum* (*Brevibacterium flavum*) AJ11564 (FERM P-5472; Japanese Patent Laid-Open (Kokai) No. 56-140895)

*Corynebacterium glutamicum* (*Brevibacterium flavum*) AJ11439 (FERM P-5136; Japanese Patent Laid-Open (Kokai) No. 56-35981)

*Corynebacterium glutamicum* H7684 (FERM BP-3004; Japanese Patent Laid-Open (Kokai) No. 04-88994)

*Corynebacterium glutamicum* (*Brevibacterium lactofermentum*) AJ11426 (FERM P-5123; Japanese Patent Laid-Open (Kokai) No. 56-048890)

*Corynebacterium glutamicum* AJ11440 (FERM P-5137; Japanese Patent Laid-Open (Kokai) No. 56-048890)

*Corynebacterium glutamicum* (*Brevibacterium lactofermentum*) AJ 11796 (FERM P-6402; Japanese Patent Laid-Open (Kokai) No. 58-158192)

Furthermore, examples of methods of imparting or enhancing the L-glutamic acid-producing ability to or in coryneform bacteria also include a method of enhancing the expression of yggB gene and a method of introducing a mutant yggB gene in which a mutation is introduced into the coding region (WO 2006/070944). That is, the bacterium may be modified so that the expression of the yggB gene is increased, or may be modified so as to have a mutant yggB gene.

The yggB gene is a gene encoding a mechanosensitive channel. Examples of the yggB gene include yggB genes of coryneform bacteria. Specific examples of the yggB genes of coryneform bacteria include yggB genes of *Corynebacterium glutamicum* ATCC 13869, *Corynebacterium glutamicum* ATCC 13032, *Corynebacterium glutamicum* ATCC 14967, and *Corynebacterium melassecola* ATCC 17965 (WO 2006/070944). The yggB gene of *Corynebacterium glutamicum* ATCC 13032 corresponds to the sequence complementary to the sequence of the nucleotide numbers 1,336,091 to 1,337,692 in the genome sequence registered as GenBank Accession No. NC 003450 in the NCBI database, and is also called NCgl1221. The YggB protein encoded by yggB gene of *Corynebacterium glutamicum* ATCC13032 is registered as GenBank accession No. NP 600492. Moreover, the nucleotide sequence of the yggB gene of *Corynebacterium glutamicum* 2256 (ATCC 13869) and the amino acid sequence of the YggB protein encoded by the gene are shown of SEQ ID NOs: 15 and 16, respectively.

A yggB gene having the "specific mutation" described herein below is also referred to as a mutant yggB gene, and a protein encoded thereby is also referred to as a mutant YggB protein. Moreover, a yggB gene not having a "specific mutation" described herein below is also referred to as a wild-type yggB gene, and a protein encoded thereby is also referred to as a wild-type YggB protein. Note, however, as for the YggB protein, the change in the amino acid sequence caused by the "specific mutation" in the yggB gene is also referred to as the "specific mutation". The term "wild-type" referred to herein is a description for convenience to distinguish it from the "mutant", and is not limited to those obtained as natural substances, as long as it does not have the "specific mutation". Examples of the wild-type YggB protein include the YggB proteins exemplified above, such as the YggB protein having the amino acid sequence shown of SEQ ID NO: 16. In addition, examples of the wild-type YggB protein also include conservative variants, which are variants in which the original function is maintained, of the YggB proteins exemplified above and the conservative variants that do not have the "specific mutation". The "original function" regarding the YggB protein may be, for example, a function as a mechanosensitive channel, or a property that improves the L-glutamic acid producing ability of the coryneform bacterium upon an increased expression in a coryneform bacterium.

The "specific mutation" is not particularly limited as long as it changes the amino acid sequence of the wild-type YggB protein such as those described above to thereby improve L-glutamic acid-producing ability of coryneform bacteria. Examples of the "specific mutation" include a mutation on a C-terminus side and a mutation in a transmembrane region (WO 2006/070944). The "specific mutation" may also be a combination of those mutations.

(1) Mutation on C-Terminus Side

The mutation on the C-terminus side is a mutation introduced into the region of the wild-type yggB gene, coding for the amino acid residues of the positions of 419 to 533 of the wild-type YggB protein. The mutation in the C-terminus side may be introduced at one or more sites in the region. The type of change in amino acid sequence induced by the mutation on the C-terminus side is not particularly limited. The mutation on the C-terminus side may be a mutation that results in, for example, substitution of amino acid residue (missense mutation), insertion of amino acid residue, deletion of amino acid residue, introduction of stop codon (nonsense mutation), frame shift mutation, or a combination thereof. The mutation on the C-terminus side can be, for example, a mutation that results in insertion of a nucleotide sequence, such as an insertion sequence (henceforth also referred to as "IS") or transposon.

Insertion of Nucleotide Sequence

Examples of the mutation on the C-terminus side include a mutation that results in insertion of a nucleotide sequence at the site coding for the valine residue at the position 419 of the wild-type YggB protein (2A-1 type mutation). The type 2A-1 type mutation may be, for example, a mutation that results in deletion or substitution of a part or all of the amino acid residues at the positions 419 to 533 of the wild-type YggB protein. Specific examples of the mutant yggB gene having the 2A-1 type mutation include the yggB gene including IS inserted into the next of "G" at the position 1255 in SEQ ID NO: 15, and thereby coding for a mutant YggB protein having the full length of 423 amino residues, which is shorter than that of the original wild-type YggB protein (SEQ ID NO: 16). The nucleotide sequence of this mutant yggB gene (V419::IS) and the amino acid sequence of a mutant YggB protein (V419::IS) encoded by the gene are shown of SEQ ID NOs: 17 and 18, respectively. In SEQ ID NO: 17, the positions 1 to 1269 correspond to CDS for this mutant YggB protein (V419::IS). Specific examples of an L-glutamic acid-producing bacterium having the mutated yggB gene (V419::IS) include the *C. glutamicum* 2256 ΔsucA ΔldhA yggB* strain (WO 2014/185430).

Substitution for Proline Residues

Examples of the mutation on the C-terminus side also include a mutation that replaces a proline residue present at positions 419 to 533 of the wild-type YggB protein with another amino acid residue. Examples of such proline residue include the proline residues at positions 424, 437, 453, 457, 462, 469, 484, 489, 497, 515, 529, and 533 of the wild-type YggB protein. Among them, the proline residue(s) at positions 424 and/or 437 can be replaced with another amino acid residue(s). The "other amino acid" is not particularly limited as long as it is a naturally occurring amino acid other than proline. Examples of the "other amino acid" include Lys, Glu, Thr, Val, Leu, Ile, Ser, Asp, Asn, Gln, Arg, Cys, Met, Phe, Trp, Tyr, Gly, Ala, and His. For example, the proline residue at position 424 may be replaced with a hydrophobic amino acid (Ala, Gly, Val, Leu or Ile), or with a branched chain amino acid residue (Leu, Val or Ile). Furthermore, for example, the proline residue at position 437 may be replaced with an amino acid residue having a hydroxyl group in the side chain (Thr, Ser, or Tyr), or with Ser.

(2) Mutation in Transmembrane Region

The YggB protein is presumed to have five transmembrane regions. The transmembrane regions correspond to the amino acid residues at positions 1 to 23 (first transmembrane region), positions 25 to 47 (second transmembrane region), positions 62 to 84 (third transmembrane region), positions 86 to 108 (fourth transmembrane region), and positions 110 to 132 (fifth transmembrane region) of the wild-type YggB protein. The mutation in a transmembrane region is a mutation in the regions coding for these transmembrane regions of the wild-type yggB gene. The mutation in a transmembrane region may be introduced into one or more sites in the regions. The mutation in a transmembrane region can be a mutation that includes substitution, deletion, addition, insertion, or inversion of one or several amino acid residues, but does not include any frame shift mutation or nonsense mutation. The term "one or several" can refer to 1 to 20, 1 to 10, 1 to 5, or 1 to 3. Examples of the mutation in a transmembrane region include a mutation that results in insertion of one or several amino acid residues (for example, Cys-Ser-Leu), between the leucine residue at position 14 and the tryptophan residue at position 15, a mutation that replaces the alanine residue at position 100 with another amino acid residue (such as an amino acid having a hydroxyl group in the side chain (Thr, Ser, or Tyr), preferably Thr)); a mutation that replaces the alanine residue at position 111 with another amino acid residue (such as a Val residue or a residue of an amino acid having a hydroxyl group in the side chain (Thr, Ser, or Tyr), preferably Val or Thr)), in the wild-type YggB protein.

The expression "an amino acid residue at position X of the wild-type YggB protein" means the amino acid residue corresponding to that of position X in SEQ ID NO: 16, unless otherwise specified. The position "X" in an amino acid sequence refers to the X-th position counted from the N-terminus of the amino acid sequence, and the amino acid residue of the N-terminus is the amino acid residue at position 1. The positions of amino acid residues indicate relative positions, and the absolute positions thereof may shift back and forth due to deletion, insertion, addition, or the like of an amino acid residue. For example, "amino acid residue at position 419 of the wild-type YggB protein" means the amino acid residue corresponding to that of the position 419 in SEQ ID NO: 16, and when one amino acid residue is deleted at a position on the N-terminus side of the position 419, the 418th amino acid residue from the N-terminus is the amino acid residue at position 419 of wild-type YggB protein". Furthermore, when one amino acid residue is inserted at a position on the N-terminus side of the position 419, the 420th amino acid residue from the N-terminus is "the amino acid residue at the position 419 of the wild-type YggB protein". Specifically, for example, amino acid residues of positions 419 to 529 of the YggB protein of *Corynebacterium glutamicum* ATCC14967 correspond to amino acid residues of positions 419 to 533 of the wild-type YggB protein.

The amino acid residue that is "the amino acid residue corresponding to that of the position X in SEQ ID NO: 16" in the amino acid sequence of an arbitrary YggB protein can be determined by aligning the amino acid sequence of the YggB protein and the amino acid sequence of SEQ ID NO: 16. The alignment can be performed by, for example, using known gene analysis software. Specific examples of such software include DNASIS manufactured by Hitachi Solutions, GENETYX manufactured by Genetyx, and the like (Elizabeth C. Tyler et al., Computers and Biomedical Research, 24 (1), 72-96, 1991; Barton G J et al. al., Journal of molecular biology, 198 (2), 327-37. 1987).

A mutant yggB gene can be obtained by modifying the wild-type yggB gene so as to have the aforementioned "specific mutation". The modification of DNA can be performed by known methods. Specific examples of the site-specific mutation method of introducing an objective mutation into a target site of DNA include a method using PCR (Higuchi, R., 61, in PCR technology, Erlich, H. A Eds., Stockton press (1989); Carter, P., Meth. In Enzymol., 154, 382 (1987)) and a method using a phage (Kramer, W. and Frits, H. J, Meth. In Enzymol., 154, 350 (1987); Kunkel, T. A. et al., Meth. In Enzymol., 154, 367 (1987)). Furthermore, the mutant yggB gene can also be obtained by chemical synthesis.

Modifying a bacterium so as to have a mutant yggB gene can be achieved by introducing the mutant yggB gene into the bacterium. Further, modifying a bacterium so as to have a mutant yggB gene can also be achieved by introducing a mutation into the yggB gene of the bacterium through natural mutation or a treatment with a mutagen.

The methods of imparting or enhancing an ability to produce an L-glutamic acid can also be effective for imparting or enhancing an ability to produce L-amino acids that are biosynthesized via L-glutamic acid as an intermediate, for example, L-glutamine, L-proline, L-arginine, L-citrulline, and L-ornithine. That is, a bacterium having an ability to produce these L-amino acids that are biosynthesized via L-glutamic acid as an intermediate may appropriately have such a property possessed by an L-glutamic acid-producing bacterium as described above. For example, a bacterium having an ability to produce these L-amino acids that are biosynthesized via L-glutamic acid as an intermediate may have been modified such that the activity of α-ketoglutarate dehydrogenase and/or succinate dehydrogenase is reduced.

<L-Glutamine-Producing Bacteria>

Examples of the method of imparting or enhancing L-glutamine producing-ability include a method of modifying a bacterium so that the activity or the activities of one or more of, for example, the L-glutamine biosynthetic enzymes. Examples of such enzymes include but are not particularly limited to, glutamate dehydrogenase (gdhA) and glutamine synthetase (glnA). The activity of glutamine synthetase may be enhanced by destruction of the glutamine adenylyltransferase gene (glnE) or destruction of the PII regulatory protein gene (glnB) (EP 1229121).

Examples of the method of imparting or enhancing the L-glutamine producing-ability also include a method of modifying a bacterium so that the activity or activities of one or more types of enzymes that catalyze a reaction branching away from the biosynthetic pathway of L-glutamine to generate a compound other than L-glutamine are reduced. Examples of such enzymes include but are not particularly limited to, glutaminase.

Specific examples of L-glutamine-producing bacteria or parent strains for inducing them include coryneform bacteria in which the activity of glutamate dehydrogenase (gdhA) and/or glutamine synthetase (glnA) are enhanced (EP1229121 and EP1424398) and coryneform bacteria in which the glutaminase activity is reduced (Japanese Patent Laid-Open (Kokai) No. 2004-187684).

Furthermore, examples of the method of imparting or enhancing L-glutamine producing-ability to or in coryneform bacteria include the method of imparting 6-diazo-5-oxo-norleucine resistance (Japanese Patent Laid-Open (Kokai) No. 3-232497), the method of imparting purine analogue resistance and methionine sulfoxide resistance (Japanese Patent Laid-Open (Kokai) No. 61-202694) and the method of imparting α-ketomalonic acid resistance (Japanese Patent Laid-Open (Kokai) No. 56-151495). Specific examples of coryneform bacteria having L-glutamine-producing ability include the following strains:

Corynebacterium glutamicum (Brevibacterium flavum) AJ 11573 (FERM P-5492; J Japanese Patent Laid-Open (Kokai) No. 56-151495)

Corynebacterium glutamicum (Brevibacterium flavum) AJ 11576 (FERM BP-10381; Japanese Patent Laid-Open (Kokai) No. 56-151495)

Corynebacterium glutamicum (Brevibacterium flavum) AJ12212 (FERM P-8123; Japanese Patent Laid-Open (Kokai) No. 61-202694)

<L-Proline Producing-Bacteria>

Examples of methods for imparting or enhancing L-proline producing-ability include a method of modifying a bacterium so that the bacterium has an increase activity of one or more of the L-proline biosynthesis enzymes. Examples of such enzymes include glutamate-5-kinase (proB), γ-glutamyl-phosphate reductase, and pyrroline-5-carboxylate reductase (putA). For enhancing the activity of such an enzyme, for example, proB gene encoding glutamate-5-kinase desensitized to feedback inhibition by L-proline (German Patent No. 3127361) can be suitably used.

Moreover, examples of methods of imparting or enhancing the L-proline producing-ability include a method of modifying a bacterium so that the bacterium has a reduced activity of an enzyme involved in decomposition of L-proline. Examples of such an enzyme include proline dehydrogenase and ornithine aminotransferase.

<L-Arginine Producing-Bacteria>

Examples of methods of imparting or enhancing L-arginine producing-ability include a method of modifying a bacterium so that the bacterium has an increased activity of one or more of, for example, the L-arginine biosynthesis enzymes. Examples of such an enzyme include, but are not limited to, N-acetyl glutamate synthase (argA), N-acetyl glutamate kinase (argB), N-acetylglutamyl phosphate reductase (argC), acetylornithine transaminase (argD), acetylornithine deacetylase (argE), ornithine carbamoyl transferase (argF, argI), argininosuccinate synthase (argG), argininosuccinate lyase (argH), ornithine acetyltransferase (argJ), carbamoyl phosphate synthase (carAB). As the N-acetylglutamate synthase (argA) gene, for example, a gene encoding a mutant N-acetylglutamate synthase that is desensitized to feedback inhibition by L-arginine by substitution for the amino acid residues corresponding to the positions 15 to 19 of the wild-type enzyme (EP1170361A) can be suitably used.

Moreover, examples of L-arginine producing bacteria or parent strains from which they can be derived include coryneform bacteria deficient in ArgR, which is an arginine repressor (US2002-0045223A) and a strain in which intracellular glutamine synthetase activity is increased (US2005-0014236A).

Furthermore, examples of L-arginine-producing bacteria or parent strains from which they can be derived include mutant strains of coryneform bacteria having resistance to amino acid analogues and the like. Examples of such strains include strains having resistance to 2-thiazolalanine and further exhibiting auxotrophy for L-histidine, L-proline, L-threonine, L-isoleucine, L-methionine or L-tryptophan (Japanese Patent Laid-Open (Kokai) No. 54-44096); a strain resistant to ketomalonic acid, fluoromalonic acid or monofluoroacetic acid (Japanese Patent Laid-Open (Kokai) No. 57-18989); a strain resistant to argininol (Japanese Patent 62-24075); a strain resistant to X-guanidine (X is a fatty chain or a derivative thereof (Japanese Patent Laid-Open (Kokai) No. 2-186995); and strains resistant to arginine hydroxamate and 6-azauracil (Japanese Patent Laid-open (Kokai) No. 57-150381). Specific examples of coryneform bacteria having L-arginine producing-ability can include the following strains:

Corynebacterium glutamicum (Brevibacterium flavum) AJ11169 (FERM BP-6892)

Corynebacterium glutamicum (Brevibacterium lactofermentum) AJ12092 (FERM BP-6906)

Corynebacterium glutamicum (Brevibacterium flavum) AJ11336 (FERM BP-6893)

Corynebacterium glutamicum (Brevibacterium flavum) AJ11345 (FERM BP-6894)

Corynebacterium glutamicum (Brevibacterium lactofermentum) AJ12430 (FERM BP-2228)

<L-Citrulline Producing-Bacteria and L-Ornithine Producing-Bacteria>

L-citrulline and L-ornithine are intermediates in the L-arginine biosynthetic pathway. Therefore, examples of methods of imparting or enhancing an ability to produce L-citrulline and/or L-ornithine include, for example, a method of modifying a bacterium to have an increased activity of one or more of the L-arginine biosynthesis enzymes. Examples of such enzymes include, but not particularly limited to, N-acetylglutamate synthase (argA), N-acetylglutamate kinase (argB), N-acetylglutamyl phosphate reductase (argC), acetylornithine transaminase (argD), acetylornithine deacetylase (argE), ornithine carbamoyl transferase (argF, argI), ornithine acetyltransferase (argJ), and carbamoyl phosphate synthase (carAB), for L-citrulline. Furthermore, examples of such enzymes include, but are not particularly limited to, N-acetylglutamate synthase (argA), N-acetylglutamate kinase (argB), N-acetylglutamyl phosphate reductase (argC), acetylornithine transaminase (argD), acetylornithine deacetylase (argE), and ornithine acetyltransferase (argJ), for L-ornithine.

An L-citrulline producing-bacterium can be easily obtained from, for example, an arbitrary L-arginine producing bacterium by decreasing the activity of argininosuccinate synthetase encoded by argG gene. Moreover, an L-ornithine producing-bacterium can be easily obtained from, for example, an arbitrary L-arginine-producing bacterium by decreasing the activity of ornithine carbamoyl transferase encoded by argF and argI genes.

Moreover, examples of methods of imparting or enhancing the L-amino acid-producing ability include, for example, a method of modifying a bacterium so as to have an increased activity for secreting an L-amino acid from bacterial cells. Such an activity for secreting an L-amino acid can be increased by, for example, increasing the expression of a gene encoding a protein responsible for secreting the L-amino acid. Examples of genes encoding the proteins responsible for secretion of various amino acids include, for example, b2682 gene (yga7), b2683 gene (ygaH), b1242 gene (ychE), and b3434 gene (yhgN) (Japanese Patent Laid-Open No. 2002-300874).

Furthermore, the method of imparting or enhancing the L-amino acid-producing ability includes, for example, a method of modifying a bacterium so as to increase the activity of a protein involved in sugar metabolism or a protein involved in energy metabolism.

Proteins involved in sugar metabolism include proteins involved in sugar uptake and glycolytic enzymes. Examples of genes encoding a protein involved in sugar metabolism include glucose 6-phosphate isomerase gene (pgi; WO 01/02542), pyruvate carboxylase gene (pyc; WO 99/18228, EP1092776A), phosphoglucomutase gene (pgm; WO 03/04598), fructose diphosphate aldolase gene (pfkB, fbp; WO 03/04664), transaldolase gene (talB; WO 03/008611), fumarase gene (fum; WO 01/02545), non-PTS sucrose uptake gene (csc; EP1149911A), sucrose assimilability gene (scrAB operon; U.S. Pat. No. 7,179,623).

Examples of genes encoding proteins involved in energy metabolism include transhydrogenase gene (pntAB; U.S. Pat. No. 5,830,716) and cytochrome bo type oxidase gene (cyoB; EP1070376A).

Moreover, methods of imparting or enhancing an ability to produce useful substances such as an L-amino acid also include, for example, a method of modifying a bacterium so as to increase the activity of phosphoketolase (WO 2006/016705). That is, the bacterium as described herein may be modified so that the activity of phosphoketolase is increased. The same method may be particularly effective for imparting or enhancing the ability to produce an L-amino acid of glutamic acid family such as an L-glutamic acid. Examples of phosphoketolases include D-xylulose-5-phosphate-phosphoketolase and fructose-6-phosphate phosphoketolase. Either or both of the D-xylulose-5-phosphate-phosphoketolase activity or the fructose-6-phosphate phosphoketolase activity may be enhanced.

The D-xylulose-5-phosphate-phosphoketolase activity refers to activity of consuming phosphoric acid to convert xylulose-5-phosphate to glyceraldehyde-3-phosphate and acetyl phosphate, and releasing one molecule of $H_2O$. This activity is measured by the method described in Goldberg, M. et al. (Methods Enzymol., 9, 515-520 (1966)) or L. Meile (J. Bacteriol. (2001) 183; 2929-2936). Examples of D-xylulose-5-phosphate phosphoketolase include bacteria belonging to *Acetobacter, Bifidobacterium, Lactobacillus, Thiobacillus, Streptococcus, Methylococcus, Butyrivibrio,* or Fibrovobacter, and yeasts belonging to the genera *Candida, Rhodotorula, Rhodosporidium, Pichia, Yarrowia, Hansenula, Kluyveromyces, Saccharomyces, Trichosporon,* and Wingea. Specific examples of D-xylulose-5-phosphate phosphoketolases and genes encoding the same are disclosed in WO 2006/016705.

In addition, fructose 6-phosphate phosphoketolase activity refers to the activity of consuming phosphoric acid to convert fructose 6-phosphate into erythrose 4-phosphate and acetyl phosphate, and releasing one molecule of $H_2O$. This activity can be measured by the method described by Racker, E. (Methods Enzymol., 5, 276-280, 1962) or the method described by the literature of L. Meile (J. Bacteriol, 183; 2929-2936, 2001). Examples of fructose 6-phosphate phosphoketolase include bacteria belonging to the genera

*Acetobacter, Bifidobacterium, Chlorobiurn, Brucella,* Methylorococcus, and *Gardnerella,* and yeasts belonging to the genera *Rhodotorula, Candida, Saccharomyces.* Specific examples of fructose 6-phosphate phosphoketolase and genes encoding the same are disclosed in WO 2006/016705.

Both phosphoketolase activities may be retained by a single enzyme (D-xylulose-5-phosphate/fructose-6-phosphate phosphoketolase).

The genes and proteins used for breeding L-amino acid producing-bacteria may have, for example, the nucleotide sequences and amino acid sequences of known genes and proteins, such as those exemplified above, respectively. In addition, genes and proteins used for breeding L-amino acid producing-bacteria may be conservative variants of known genes and proteins, such as those exemplified above, respectively. Specifically, for example, the genes used for breeding L-amino acid producing-bacteria may each encode a protein having an amino acid sequence of a known protein, but can include substitution, deletion, insertion, or addition of one or several amino acid residues at one or several positions, so long as the original function of the encoded protein is maintained. For conservative variants of genes and proteins, the descriptions concerning conservative variants of the target genes and target proteins described below can be similarly applied.

<1-2> Specific Properties

The bacterium is modified so as to have specific properties. The bacterium can be obtained by modifying a bacterium having an L-amino acid-producing ability so as to have specific properties. Furthermore, the bacterium can also be obtained by imparting or enhancing the L-amino acid-producing ability after modifying the bacterium so as to have specific properties. Note, however, the bacterium may have acquired an L-amino acid-producing ability by being modified so as to have specific properties. The bacterium suitably has, for example, the properties possessed by L-amino acid producing-bacteria as described above, in addition to being modified so as to have specific properties. The modifications constructing the bacterium of the invention can be made in any order.

Modifying a bacterium so as to have specific properties enables improvement in L-amino acid-producing ability of the bacterium, i.e., enhancement of L-amino acid production by the bacteria. Examples of the "enhancement of L-amino acid production" include an increase (enhance) in the amount of L-amino acid accumulated in a culture medium.

Specific properties include a modification for increasing intracellular oxaloacetic acid (OAA) pool. The term "increasing intracellular oxaloacetic acid (OAA) pool" may refer to an increase in the amount of oxaloacetic acid (OAA) accumulated in cells.

Moreover, specific properties include a modification for increasing availability of a carbon source via the phosphoketolase pathway. The term "increasing availability of a carbon source via the phosphoketolase pathway" may refer to an increase in a flux of the phosphoketolase pathway (i.e., the amount of carbon source metabolized via the phosphoketolase pathway) and/or reduction of the amount of byproducts accumulated that can be produced from the carbon source metabolized via the phosphoketolase pathway. The byproducts include acetic acid. Acetic acid can be accumulated, for example, due to an increased flux in the phosphoketolase pathway. Examples of the modification for increasing availability of a carbon source via the phosphoketolase pathway include a modification for increasing a flux of the phosphoketolase pathway and a modification for increasing assimilation of acetic acid.

Furthermore, the specific properties include the following modifications:

(A) a modification for increasing activity of acetate kinase;

(B) a modification for increasing activity of fructose-1,6-bisphosphatase;

(C) a modification for decreasing activity of pyruvate dehydrogenase;

(D) a modification for decreasing activity of aspartate transaminase; and (E) a modification for decreasing activity of malic enzyme.

The modifications (D) and (E) above each can be one example of modifications for increasing intracellular oxaloacetic acid (OAA) pool. The modifications (A), (B), and (C) above each can be one example of modifications for increasing availability of a carbon source via the phosphoketolase pathway. The modifications (A) and (C) above each can be one example of modifications specifically for improving assimilation of acetic acid. The modification (B) above can be one example of a modification specifically for increasing a flux of the phosphoketolase pathway.

The bacterium may have one or more properties selected from the properties exemplified above.

The bacterium may have, for example, a modification for increasing intracellular oxaloacetic acid (OAA) pool and/or a modification for increasing availability of a carbon source via the phosphoketolase pathway. The bacterium, for example, may have at least a modification for increasing availability of a carbon source via phosphoketolase pathway. That is, specifically the bacteria may only have, for example, the modification for increasing availability of a carbon source via the phosphoketolase pathway, among the modification for increasing intracellular oxaloacetic acid (OAA) pool and the modification for increasing availability of a carbon source via the phosphoketolase pathway, or it may have a combination of the modification for increasing availability of a carbon source via the phosphoketolase pathway and the modification for increasing intracellular oxaloacetic acid (OAA) pool.

The bacterium may have, for example, a modification for increasing intracellular oxaloacetic acid (OAA) pool, a modification for increasing a flux of the phosphoketolase pathway and/or a modification for increasing assimilation of acetic acid. The bacterium, for example, may have at least a modification for increasing assimilation of acetic acid. That is, specifically the bacterium may only have, for example, the modification for increasing assimilation of acetic acid, among the modification for increasing intracellular oxaloacetic acid (OAA) pool, the modification for increasing a flux of the phosphoketolase pathway and the modification for increasing assimilation of acetic acid, or it may have a combination of the modification for increasing assimilation of acetic acid and the modification for increasing intracellular oxaloacetic acid (OAA) pool and/or the modification for increasing a flux of the phosphoketolase pathway.

The bacterium may have one or more, for example, one, two, three, four, or all five, modifications (A) to (E) as described above. The bacterium may specifically have, for example, (A), (B), (C), (D), (E), (A)+(B), (A)+(C), (A)+(D), (A)+(E), (B)+(C), (B)+(D), (B)+(E), (C)+(D), (C)+(E), (D)+(E), (A)+(B)+(C), (A)+(B)+(D), (A)+(B)+(E), (A)+(C)+(D), (A)+(D)+(E), (B)+(C)+(D), (B)+(C)+(E), (B)+(D)+(E), (C)+(D)+(E), (A)+(B)+(C)+(D), (A)+(B)+(C)+(E), (A)+(B)+(D)+(E), (A)+(C)+(D)+(E), (B)+(C)+(D)+(E), (A)+(B)+(C)+(D)+(E). The term "(A)+(B) modifications" refers to a combination of the modification (A) and the modification (B). This description can be similarly applied to other combinations. The bacterium, for example, may have at least the modification (A) as described above. That is, specifically, the bacterium may have, for example, only the modification (A), or modification (A) and one or more of the modifications (B) to (E), for example, combinations of one, two, three, or all four modifications thereof. The bacterium may also have, for example, at least the modification (B) above.

The term "aspartate transaminase" may refer to a protein having an activity catalyzing an aminotransfer reaction of aspartic acid and/or glutamic acid (for example, EC 2.6.1.1). The same activity is also referred to as "aspartate transaminase activity." The aspartate transaminase activity may specifically be an activity catalyzing a reaction that converts L-aspartate and α-ketoglutarate to oxaloacetate and L-glutamate and/or the reverse. Aspartate transaminase is also referred to as "glutamic-oxaloacetic transaminase". The gene encoding aspartate transaminase is also referred to as "aspartate transaminase gene." Examples of the aspartate transaminase gene include aspT gene. The nucleotide sequence of the aspartate transaminase gene such as aspT gene possessed by the bacterium to be modified and the amino acid sequence of the aspartate transaminase such as AspT protein encoded by the gene, can be obtained from public databases such as NCBI. The nucleotide sequence of aspT gene (CGBL 0102840) of *Corynebacterium glutamicum* ATCC 13869 and the amino acid sequence of the protein encoded by the gene are shown as SEQ ID NOs: 1 and 2, respectively.

The term "malic enzyme" may refer to a protein having an activity catalyzing oxidative decarboxylation of malic acid (for example, EC EC 1.1.1.38, EC 1.1.1.39, or EC 1.1.1.40). The same activity is also referred to as "malic enzyme activity". The malic enzyme activity may specifically be an activity catalyzing a reaction that decarboxylates malic acid to produce pyruvic acid in the presence of electron acceptors. The electron acceptors include NAD and NADP'. The malic enzymes may only be able to utilize at least one electron acceptor. The malic enzyme may also have an activity catalyzing a decarboxylation reaction of oxaloacetic acid (specifically, a reaction of converting oxaloacetic acid to pyruvic acid and carbon dioxide). The malic enzyme is also referred to as "malate dehydrogenase". The gene encoding the malic enzyme is also referred to as a "malic enzyme gene." The malic enzyme genes include malE gene. The nucleotide sequence of the malic enzyme gene such as malE gene possessed by the bacterium to be modified and the amino acid sequence of the malic enzyme such as a MalE protein encoded by the gene, can be obtained, for example, from public databases such as NCBI. The nucleotide sequence of malE gene (CGBL 0129850) of *Corynebacterium glutamicum* ATCC 13869 and the amino acid sequence of the protein encoded by the gene are shown as SEQ ID NOs: 3 and 4, respectively.

The term "pyruvate dehydrogenase" may refer to a protein having an activity catalyzing oxidative decarboxylation of pyruvic acid (for example, EC 1.2.5.1). The same activity is also referred to as "pyruvate dehydrogenase activity". The pyruvate dehydrogenase activity may specifically be an activity catalyzing a reaction that decarboxylates pyruvic acid to produce acetic acid in the presence of electron acceptors. The electron acceptors include quinones such as ubiquinone. The pyruvate dehydrogenase may only be able to utilize at least one electron acceptor. The gene encoding the pyruvate dehydrogenase is also referred to as a "pyruvate dehydrogenase gene." The pyruvate dehydrogenase genes include poxB gene. The nucleotide sequence of the pyruvate dehydrogenase gene such as poxB gene possessed by the bacterium to be modified and the amino acid sequence of the pyruvate dehydrogenase such as PoxB protein encoded by them, can be obtained, for example, from public databases such as NCBI. The nucleotide sequence of poxB gene (CGBL_0125410) of *Corynebacterium glutamicum* ATCC 13869 and the amino acid sequence of the protein encoded by the gene are shown as SEQ ID NOs: 5 and 6, respectively.

The term "acetate kinase" may refer to a protein having an activity catalyzing a phosphorylation reaction of acetic acid (for example, EC 2.7.2.1). The same activity is also referred to as "acetate kinase activity". The acetate kinase activity may specifically be an activity catalyzing a reaction that phosphorizes acetic acid to produce acetyl phosphoric acid in the presence of phosphate donors. The phosphate donors include ATP. The acetate kinase may only be able to utilize at least one phosphate donor. The gene encoding the acetate kinase is also referred to as an "acetate kinase gene." The acetate kinase genes include ack gene. The acetate kinase genes such as ack gene include genes of various organisms such as coryneform bacteria and bacteria belonging to the Enterobacteriaceae family. Specific examples of the ack gene include ack gene of *Corynebacterium glutamicum* and *E. coli*. The nucleotide sequence of the acetate kinase gene such as ack genes of various organisms and the amino acid sequence of the acetate kinase such as Ack protein encoded by the gene, can be obtained, for example, from public databases such as NCBI. The nucleotide sequence of ack gene (CGBL_0126910) of *Corynebacterium glutamicum* ATCC 13869 and the amino acid sequence of the protein encoded by the gene are shown of SEQ ID NOs: 7 and 8, respectively. The nucleotide sequence of ack gene of *E. coli* MG1655 and the amino acid sequence of the protein encoded by the gene are shown as SEQ ID NOs: 9 and 10, respectively.

The term "fructose 1,6-bisphosphatase" may refer to a protein having an activity catalyzing a dephosphorylation reaction of fructose-1,6-bisphosphate (for example, EC 3.1.3.11). The same activity is also referred to as "fructose-1,6-bisphosphatase activity." The fructose-1,6-bisphosphatase activity may specifically be an activity catalyzing a reaction of converting fructose-1,6-bisphosphate to fructose-6-phosphate. The gene encoding fructose-1,6-bisphosphatase is also referred to as the "fructose-1,6-bisphosphatase gene." The fructose-1,6-bisphosphatase genes include glpX gene. Examples of fructose-1,6-bisphosphatase genes such as the glpX gene include those of various organisms such as coryneform bacteria and bacteria belonging to the Enterobacteriaceae family. Specific examples of the glpX genes include those of *Corynebacterium glutamicum* and *E. coli*. The nucleotide sequences of the fructose-1,6-bisphosphatase genes such as glpX genes of various organisms and the amino acid sequence of the fructose-1,6-bisphosphatase such as GlpX protein encoded by the gene, can be obtained from public databases such as NCBI. The nucleotide sequence of glpX gene (NCg10976) of *Corynebacterium glutamicum* ATCC 13032 and the amino acid sequence of the protein encoded by the gene are shown of SEQ ID NOs: 11 and 12, respectively. The nucleotide sequence of glpX gene of *E. coli* MG1655 and the amino acid sequence of the protein encoded by the gene are shown as SEQ ID NOs: 13 and 14, respectively.

A method of reducing an activity of a protein will be described below. The activity of a protein can be reduced, for example, by decreasing expression of a gene encoding the protein or by disrupting the gene. Such methods of reducing the activity of a protein can be used singly or appropriately combined for use.

A method of increasing an activity of a protein will be discussed below. The activity of a protein can be increased, for example, by increasing expression of a gene encoding the protein. The expression of the gene can be increased, for example, by increasing the copy number of the gene or by modifying an expression regulatory sequence of a gene. Such methods of increasing the activity of a protein can be used singly or appropriately combined for use.

Proteins in which their activities are reduced or increased in specific properties are also collectively referred to as "target proteins." The genes encoding target proteins are also collectively referred to as "target genes."

The target gene may be, for example, a gene having a nucleotide sequence of the target gene exemplified above (for example, the nucleotide sequence shown of SEQ ID NO: 1, 3, 5, 7, 9, 11, or 13). The target protein may be, for example, a protein having the amino acid sequence of the target protein exemplified above (for example, the amino acid sequence shown of SEQ ID NO: 2, 4, 6, 8, 10, 12, or 14). The description "having the (amino acid or nucleotide) sequence" refers to "containing the (amino acid or nucleotide) sequence" and includes including the (amino acid or nucleotide) sequence" unless otherwise specified.

The target gene may be a variant of the target gene exemplified above (for example, a gene having a nucleotide sequence shown of SEQ ID NO: 1, 3, 5, 7, 9, 11, or 13) as long as the original function is maintained. Similarly, the target protein may be a variant of the target protein exemplified above, for example, a protein having an amino acid sequence shown of SEQ ID NO: 2, 4, 6, 8, 10, 12, or 14, as long as the original function is maintained. Such variants in which the original function is maintained may be referred to as "conservative variants." The terms "aspT gene," "malE gene," "poxB gene," "ack gene," and "glpX gene" shall encompass their conservative variants, in addition to the aspT gene, malE gene, poxB gene, ack gene, and glpX gene, which were exemplified above. Similarly, the terms "AspT protein," "MalE protein," "PoxB protein," "Ack protein," and "GlpX protein" shall encompass their conservative variants, in addition to the aspT protein, MalE protein, PoxB protein, Ack protein, and GlpX proteins, which were exemplified above. Examples of the conservative variants include homologues or artificially modified versions of the target genes and target proteins exemplified above.

The term "original function is maintained" means that a variant of gene or protein has a function (for example, activity or property) corresponding to the function (for example, activity or property) of the original gene or protein. The expression "the original function is maintained" for a gene means that a variant of the gene encodes a protein, the original function of which is maintained. That is, the expression "the original function is maintained" for each target gene means that a variant of the gene encodes a protein having the activity of each target protein: aspartate transaminase activity in relation to aspartate transaminase; malic enzyme activity in relation to malic enzyme; pyruvate dehydrogenase activity in relation to pyruvate dehydrogenase; acetate kinase activity in relation to acetate kinase; fructose-1,6-bisphosphatase activity in relation to fructose-1,6-bisphosphatase. Moreover, the "original function is maintained" for each target protein means that a variant of the protein has the following activities of each target protein: aspartate transaminase activity in relation to aspartate transaminase; malic enzyme activity in relation to malic enzyme; pyruvate dehydrogenase activity in relation to pyruvate dehydrogenase; acetate kinase activity in relation to acetate kinase; fructose-1,6-bisphosphatase activity in relation to fructose-1,6-bisphosphatase.

The aspartate transaminase activity can be measured, for example, by incubating an enzyme with the corresponding substrate, for example, L-aspartic acid and α-ketoglutaric acid, and measuring enzyme- and substrate-dependent uptake of the corresponding products, for example, oxalo-acetic acid and L-glutamic acid.

The malic enzyme activity can be measured, for example, by incubating an enzyme with the corresponding substrate, for example, malic acid in the presence of electron acceptors and measuring enzyme- and substrate-dependent uptake of the corresponding product, for example, pyruvic acid.

The pyruvate dehydrogenase activity can be measured, for example, by incubating an enzyme with the corresponding substrate, for example, pyruvate, in the presence of an electron acceptor and measuring enzyme- and substrate-dependent uptake of the corresponding product, for example, acetic acid.

The acetate kinase activity can be measured, for example, by incubating an enzyme with the corresponding substrate, for example, acetic acid, in the presence of a phosphate group donor and measuring enzyme- and substrate-dependent uptake of the corresponding product, for example, acetyl phosphate.

The fructose-1,6-bisphosphatase activity can be measured, for example, by incubating an enzyme with the corresponding substrate, for example, fructose-1,6-bisphosphate, and measuring enzyme- and substrate-dependent uptake of the corresponding product, for example, fructose-6-phosphate.

Conservative variants will be exemplified below.

Homologs of target genes or target proteins can be easily obtained from public databases by, for example, a BLAST search or FASTA search, using any of the nucleotide sequences of the target genes or amino acid sequences of the target proteins, exemplified above as query sequences. The homologs of target genes can also be obtained by, for example, PCR using a chromosome of various organisms as the template, and oligonucleotides prepared on the basis of any of the nucleotide sequences of these publicly known target genes as primers.

The target gene may be a gene encoding a protein having any of the aforementioned amino acid sequences in which one or several amino acids at one or several positions have been substituted, deleted, inserted, and/or added in the above amino acid sequence, for example, the amino acid sequence shown of SEQ ID NO: 2, 4, 6, 8, 10, 12, or 14, as long as the original function is maintained. For example, the N-terminus and/or the C-terminus of the encoded protein may be elongated or shortened. Note, however, the above "one or several" refers to, for example, 1 to 50, 1 to 40, 1 to 30, 1 to 20, 1 to 10, 1 to 5, or 1 to 3, depending on the position and type of amino acid residues in the three-dimensional structure of the protein.

The aforementioned substitution, deletion, insertion, and/or addition of one or several amino acid residues can be a conservative mutation that maintains the normal function of the protein. Typical examples of the conservative mutation are conservative substitutions. The conservative substitution is a mutation wherein substitution takes place mutually among Phe, Trp, and Tyr, if the substitution site is an aromatic amino acid; among Leu, Ile, and Val, if it is a hydrophobic amino acid; between Gln and Asn; if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions can include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Furthermore, such substitution, deletion, insertion, or addition of amino acid residues as described above can include a naturally occurring mutation due to an individual difference, or a difference of species of the organism from which the gene is derived (mutant or variant).

Moreover, the target gene may be a gene encoding a protein having an amino acid sequence having an identity of, for example, 50% or more, 65% or more, or 80% or more, preferably 90% or more, 95% or more, 97% or more, or 99% or more, to the total amino acid sequence of any of the aforementioned amino acid sequences, so long as the original function is maintained.

The target gene may also be a gene, for example, DNA, that is able to hybridize under stringent conditions with a probe that can be prepared from any of the aforementioned nucleotide sequences, for example, the nucleotide sequence shown of SEQ ID NO: 1, 3, 5, 7, 9, 11, or 13, such as a sequence complementary to a partial or entire sequence of any of the aforementioned nucleotide sequences, so long as the original function is maintained. The term "stringent conditions" can refer to conditions under which a so-called specific hybrid is formed, and a non-specific hybrid is not formed. Examples of stringent conditions can include those under which highly homologous DNAs hybridize to each other, for example, DNAs not less than 50% or more, 65% or more, or 80% or more, 90% or more, 95% or more, 97% or more, or 99% or more homologous, and DNAs less homologous than the above do not hybridize to each other, or conditions of washing of typical Southern hybridization, i.e., conditions of washing once, or 2 or 3 times, at a salt concentration and temperature corresponding to 1×SSC, 0.1% SDS at 60° C.; SSC, 0.1% SDS at 60° C.; or 0.1×SSC, 0.1% SDS at 68° C.

The probe used for the aforementioned hybridization may be a part of a sequence that is complementary to the gene as described above. Such a probe can be prepared by PCR using oligonucleotides prepared on the basis of a known gene sequence as primers and a DNA fragment containing any of the aforementioned genes as a template. As the probe, for example, a DNA fragment having a length of about 300 bp can be used. When a DNA fragment having a length of about 300 bp is used as the probe, the washing conditions of the hybridization may be, for example, 50° C., 2×SSC and 0.1% SDS.

Furthermore, since the degeneracy of codons differs depending on the host, the target gene may be such that arbitrary codons may be replaced with respective equivalent codons. That is, the target gene may be a variant of any of the target genes exemplified above due to the degeneracy of the genetic code. For example, the target gene may be modified so as to have optimal codons according to frequency of codon use in a host.

Incidentally, the "identity" between amino acid sequences refers an identity between amino acid sequences calculated by blastp, using the default settings of Scoring Parameters (Matrix: BLOSUM62; Gap Costs: Existence=11, Extension=1; Compositional Adjustments: Conditional compositional score matrix adjustment). The "identity" between amino acid sequences refers to an identity between amino acid sequences calculated by blastn, using the default settings of Scoring Parameters (Match/Mismatch Scores=1,–2; Gap Costs=Linear).

Incidentally, the aforementioned descriptions regarding conservative variants of the genes or proteins can be similarly applied to variants of arbitrary proteins, such as L-amino acid biosynthesis system enzymes and genes which encode them.

<1-3> Method of Increasing Protein Activity

Hereinafter, a method of increasing the activity of a protein will be described.

The expression "the activity of a protein is increased" means that the activity of the protein is increased as compared to an unmodified strain. The expression "the activity of a protein is increased" may specifically mean that the activity of the protein per cell is increased as compared to an unmodified bacterial strain. As used herein, the term "unmodified strain" or "unmodified bacterium" refers to a control strain that has not been modified so as to increase the activity of the target protein. Examples of the unmodified strains include a wild-type strain and a parental strain. Specific examples of the unmodified strain include the corresponding strain of each bacterial species. In addition, specific examples of the unmodified strain include strains exemplified in the description of bacteria. That is, in one aspect, the activity of a protein may be increased relative to a reference strain (i.e., a corresponding strain of the species to which the bacterium belongs). Moreover, in another embodiment, the activity of a protein may be increased as compared to the *C. glutamicum* ATCC 13869 strain. Further, in another embodiment, the activity of a protein may be increased as compared to the *C. glutamicum* ATCC 13032 strain. Further, in another embodiment, the activity of a protein may be increased as compared to the *C. glutamicum* AJ12036 (FERM BP-734). Moreover, in another embodiment, the activity of a protein may be increased as compared to the *C. glutamicum* YDK010 strain. Incidentally, the expression "activity of a protein is increased" is referred to as "activity of a protein is enhanced". More specifically, the expression "the activity of a protein is increased" means that the number of molecules of the same protein per cell is increased as compared to an unmodified strain, and/or the function of the same protein per molecule is increased. That is, "activity" in the case of "the activity of a protein is increased" may refer to not only the catalytic activity of a protein but also the transcription amount (mRNA amount) or the translation amount (the amount of protein) of the gene encoding the protein. "The number of molecules per cell of the protein" may refer to an average value of the number of molecules of the protein per cell. Further, the expression "the activity of a protein is increased" refers to not only increasing the activity of the target protein in the strain originally having the activity of the target protein, but also imparting the activity of the same protein in the strain in which the activity of the target protein originally is not present. Moreover, as long as an increase in the activity of a protein results, the activity of the target protein inherently present in a host may be attenuated or eliminated, and then the activity of the protein of the suitable target may be imparted.

The degree of the increase in the activity of a protein is not particularly limited as long as the activity of the protein is increased as compared to an unmodified strain. The activity of the protein may be increased, for example, by 1.5 times or more, 2 times or more, or 3 times or more of that of an unmodified strain. In addition, when the unmodified strain does not have the activity of the target protein, the same protein may be produced by introducing a gene encoding the same protein. For example, the activity of the same protein may be produced to the extent where the activity thereof can be measured.

The modification for increasing the activity of a protein can be achieved by, for example, increasing the expression of a gene encoding the protein. The phrase "the expression of a gene is increased" means that the expression of the gene is increased as compared to an unmodified strain such as a wild-type strain or a parent strain. Specifically, the phrase "the expression of a gene is increased" means that the amount of expression of the gene per cell is increased as compared to that of an unmodified strain. The term "the amount of expression of the gene per cell" may refer to an average value of the amounts of expression of the genes per cell. More specifically, the phrase "the expression of a gene is increased" means that the transcription amount (the amount of mRNA) of the gene is increased and/or the translation amount (the amount of the protein) of the gene is increased. Note, however, the phrase "the expression of a gene is increased" is also referred to as "expression of a gene is enhanced." The expression of a gene may be increased, for example, 1.5 times or more, 2 times or more, or 3 times or more of that of an unmodified strain. Furthermore, the phrase "the expression of a gene is increased" encompasses not only raising the expression amount of the gene in the strain in which the target gene is originally expressed, but also expressing the gene in a strain in which the target gene is not originally expressed. That is, the phrase "the expression of a gene is increased" may also refer, for example, introducing the gene into a strain not retaining the target gene and expressing the gene.

An increase in expression of a gene can be achieved, for example, by increasing the copy number of the gene.

The copy number of a gene can be increased by introducing the gene into a chromosome of a host. A gene can be introduced into a chromosome by, for example, using homologous recombination (Miller, J. H Experiments in Molecular Genetics, 1972, Cold Spring Harbor Laboratory). Examples of a gene introduction method utilizing homologous recombination include, for example, a method using a linear DNA, such as Red-driven integration (Datsenko, K. A, and Wanner, B. L Proc. Natl. Acad. Sci. U.S.A. 97: 6640-6645 (2000)), a method of using a plasmid containing a temperature sensitive replication origin, a method of using a plasmid capable of conjugative transfer, a method of using a suicide vector not having a replication origin that functions in a host, a transduction method using phages. Specifically, a gene can be introduced on a chromosome of a host by transforming the host with recombinant DNA containing a target gene to cause homologous recombination with the target site on the chromosome of the host. The structure of the recombinant DNA used for homologous recombination is not particularly limited as long as homologous recombination occurs in the desired manner. For example, a host is transformed with linear DNA containing a target gene and having homologous nucleotide sequences upstream and downstream of the target gene on the chromosome at both ends of the gene to cause homologous recombination upstream and downstream of the target site, respectively, thereby enabling replacement of the target site with the gene. The recombinant DNA used for homologous recombination may have a marker gene for selecting transformants. Only one copy, or two or more copies of a gene may be introduced. For example, a large number of copies of a gene can be introduced into a chromosome by homologous recombination targeting an amino acid sequence that has a large number of copies on the chromosome. Examples of the amino acid sequence that has a large number of copies on a chromosome include repetitive DNA sequence and inverted repeats at both ends of a transposon. In addition, the homologous recombination may be performed by targeting appropriate sequences on a chromosome, such as a gene unnecessary for production of a target substance. Moreover, a gene can also be randomly introduced on a chromosome by using a transposon or Mini-Mu (Japanese Patent Laid-Open (Kokai) No. 2-109985, US Pat. EP805867B1). Incidentally, the method of modifying chromosomes utilizing such homologous recombination is not limited to introduction of target genes, but can be used for arbitrary modifications of chromosomes, such as a modification of expression regulatory sequences.

Introduction of a target gene into a chromosome can be confirmed by Southern hybridization using a probe having a sequence complementary to the whole gene or a part thereof, PCR using primers prepared based on the sequence of the gene, or the like.

Moreover, an increase in the copy number of a gene can also be achieved by introducing a vector containing the gene into a host. For example, the copy number of a target gene can be increased by ligating a DNA fragment containing the target gene with a vector that functions in a host to construct an expression vector of the gene, and transforming the host with the expression vector. The DNA fragment containing the target gene can be obtained by, for example, PCR using the genomic DNA of a microorganism having the target gene as the template. As the vector, a vector capable of autonomous replication in host cells can be used. The vector can be a multi-copy vector. In order to select transformants as well, the vector can have a marker such as an antibiotic resistance gene. Furthermore, the vector may have a promoter or terminator for expressing the inserted gene. The vector may be, for example, a vector derived from a bacterial plasmid, a vector derived from a yeast plasmid, a vector derived from a bacteriophage, cosmid, phagemid, or the like. Specific examples of vectors capable of autonomous replication in coryneform bacteria, include pHM1519 (Agric. Biol. Chem., 48, 2901-2903 (1984)); pAM330 (Agric. Biol. Chem., 48, 2901-2903 (1984)); plasmids with drug resistance genes, modified therefrom; pCRY30 (Japanese Patent Laid-Open (Kokai) No. 3-210184); pCRY21, pCRY2KE, pCRY2KX, pCRY31, pCRY3KE, and pCRY3KX (Japanese Patent Laid-Open (Kokai) No. 2-72876, U.S. Pat. No. 5,185, 262); pCRY2 and pCRY3 (Japanese Patent Laid-Open (Kokai) No. 1-191686); pAJ655, pAJ611, and pAJ1844 (Japanese Patent Laid-Open (Kokai) No. 58-192900); pCG1 (Japanese Patent Laid-Open (Kokai) No. 57-134500); pCG2 (Japanese Patent Laid-Open (Kokai) No. 58-35197); pCG4 and pCG11 (Japanese Patent Laid-Open (Kokai) No. 57-183799); pVK7 (Japanese Patent Laid-Open (Kokai) No. 10-215883); pVK9 (US2006-0141588); pVC7 (Japanese Patent Laid-Open (Kokai) No. 9-070291); pVS7 (WO 2013/069634).

When a gene is introduced, it is sufficient that the gene is able to be expressed by a host. Specifically, it is sufficient that the gene is harbored by a host so that it is expressed under control by a promoter that functions in the host. The promoter is not particularly limited so long as it is able to function in the host. The term "promoter that is able to function in a host" can refer to a promoter that shows a promoter activity in the host. The promoter may be a promoter derived from the host, or a heterogenous promoter. The promoter may be the native promoter of the gene to be introduced, or a promoter of another gene. As the promoter, for example, such a stronger promoter as will be described below may also be used.

A terminator for termination of gene transcription may be located downstream of the gene. The terminator is not particularly limited so long as it functions in the host. The terminator may be a terminator derived from the host, or a heterogenous terminator. The terminator may be the native terminator of the gene to be introduced, or a terminator of another gene.

Vectors, promoters, and terminators available in various microorganisms are described in detail in "Fundamental Microbiology Vol. 8, Genetic Engineering, KYORITSU SHUPPAN CO., LTD, 1987", and those can be used.

Moreover, when two or more genes are introduced, each gene may be expressively harbored by the host. For example, each gene may be present in a single expression vector, or all may be present on a chromosome. Furthermore, each gene may be separately present in a plurality of expression vectors, or may be separately present in a single or a plurality of expression vectors and on a chromosome. Alternatively, an operon may be constructed and introduced by two or more genes. Examples of the phrase "in the case of introducing two or more genes" include a case in which a gene encoding each of two or more proteins (for example, enzymes) is introduced, a case in which a gene encoding each of two or more subunits constitute a single protein complex (for example, enzyme complex), is introduced, and combinations thereof.

The gene to be introduced is not particularly limited as long as it encodes a protein that is able to function in the host. The gene to be introduced may be a gene native to the host or a heterologous gene. The gene to be introduced can be obtained by, for example, PCR using primers designed based on the nucleotide sequence of the gene, and using the genomic DNA of an organism having the gene, a plasmid carrying the gene, or the like, as a template. Moreover, the gene to be introduced may be totally synthesized, for example, based on the nucleotide sequence of the gene (Gene, 60 (1), 115-127 (1987)). The obtained gene can be used as is or after being appropriately modified. Namely, the variant can be obtained by modifying the gene. Modification of the gene can be performed by known methods. For example, a target mutation can be introduced into a target site of DNA by the site-specific mutation method. That is, the coding region of a gene can be modified by the site-specific mutation method so that a specific site of the encoded protein can include substitution, deletion, insertion, and/or addition of amino acid residues. Examples of the site-specific mutation method include the method using PCR (Higuchi, R., 61, in PCR technology, Erlich, H. A Eds., Stockton press (1989); Carter, P., Meth. In Enzymol., 154, 382 (1987)) and methods using phage (Kramer, W. and Frits, H. J, Meth. In Enzymol., 154, 350 (1987); Kunkel, T. A et al., Meth. In Enzymol., 154, 367 (1987)). Alternatively, a variant of a gene may be totally synthesized.

Note, however, when a protein functions as a complex made up of a plurality of subunits, all of the subunits may be modified or only a portion may be modified as long as the activity of the protein is increased as a result. That is, for example, when the activity of a protein is increased by increasing the expression of a gene, the expression of all of the genes encoding those subunits may be enhanced, and only a part of the expression may be enhanced. The expression of all of the genes encoding those subunits is usually enhanced. Moreover, each subunit making up the complex may be native to a single type of organism, or two or more different types of organisms, as long as the complex has the function of the target protein. That is, for example, genes of the same organism encoding a plurality of subunits may be introduced into a host, or genes of different organisms encoding a plurality of subunits may be introduced into a host.

Furthermore, an increase in the gene expression can be achieved by improving the transcription efficiency of the gene. Moreover, the increase in the gene expression can be achieved by improving the translation efficiency of the gene. The improvements in the transcription efficiency and the translation efficiency of a gene can be achieved, for example, by modification of expression regulatory sequence of the gene. The term "expression regulatory sequence" collectively refers to sites that affect expression of a gene. Examples of the expression regulatory sequence include a promoter, Shine-Dalgarno (SD) sequence (also referred to as ribosome binding site (RBS)), and a spacer region between RBS and the start codon. Expression regulatory sequences can be identified by using a promoter search vector or gene analysis software such as GENETYX. The modification of these expression regulatory sequences can be performed by, for example, a method of using a temperature sensitive vector, or by a Red driven integration method (WO 2005/010175).

The improvement in transcription efficiency of a gene can be achieved by, for example, replacing the promoter of the gene on a chromosome with a stronger promoter. The term "stronger promoter" refers to a promoter that improves transcription of a gene with an inherent wild-type promoter of a gene. Examples of stronger promoters that can be used in coryneform bacteria include artificially modified P54-6 promoter (Appl. Microbiol. Biotechnol., 53, 674-679 (2000)), pta, aceA, aceB, adh, amyE promoters which can be induced in coryneform bacteria with acetic acid, ethanol, pyruvate, and the like, cspB, SOD, tuf (EF-Tu) promoters, which are strong promoters with a large expression amount in coryneform bacteria (Journal of Biotechnology 104 (2003) 311-323, Appl Environ Microbiol. 2005 December; 71 (12): 8587-96.), as well as lac promoter, a tac promoter, a trc promoter. Moreover, as the stronger promoter, a highly-active inherent promoter may also be obtained by using various reporter genes. For example, by making the −35 and −10 regions in a promoter region closer to the consensus sequence, the activity of the promoter can be enhanced (WO 00/18935). Examples of the highly active promoter include various tac-like promoters (Katashkina J I et al. Russian Federation Patent application 2006134574) and pnlp8 promoter (WO 2010/027045). Methods of evaluating the strength of promoters and examples of strong promoters can be found in the paper of Goldstein et al. (Prokaryotic promoters in biotechnology. Biotechnol. Annu. Rev., 1, 105-128 (1995)) and the like.

An improvement in the translational efficiency of a gene can be achieved, for example, by replacing the Shine-Dalgano (SD) sequence (also referred to as ribosome binding site (RBS)) of the gene on a chromosome with a stronger SD sequence. The "stronger SD sequence" refers to an SD sequence that improves translation of mRNA compared with the inherent wild-type SD sequence of the gene. Examples of stronger SD sequences include RBS of the gene 10 derived from phage T7 (Olins P. O. et al, Gene, 1988, 73, 227-235). Furthermore, it is known that substitution, insertion, or deletion of several nucleotides in a spacer region between the RBS and the start codon, in particular a sequence immediately upstream of the start codon (5'-UTR), significantly affects the stability and translation efficiency of the mRNA, and the modification of these can also improve gene translation efficiency.

The improvement of the translation efficiency of a gene can also be achieved, for example, by modification of codons. For example, the translation efficiency of the gene can be improved by replacing a rare codon present in the gene with more frequently used synonymous codons. That is, the gene to be introduced may be modified, for example, so as to contain optimal codons, according to a usage frequency of codons observed in the chosen host. Codon can be replaced by for example, the site-specific mutation. Moreover, a gene fragment in which target codons have been replaced may be totally synthesized. The usage frequency of codons in various organisms can be found in "Codon Usage Database" (http://www.kazusa.or.jp/codon; Nakamura, Y. et al, Nucl. Acids Res., 28, 292 (2000)).

Furthermore, an increase in gene expression can also be achieved by amplifying a regulator that increases gene expression, or by deleting or attenuating a regulator that reduces gene expression.

The techniques for increasing the expression of genes as described above may be used singly or in any combination.

Alternatively, the modifications increasing the activity of a protein can also be achieved by, for example, enhancing the specific activity of the protein. Enhancement of specific activity also includes desensitization to feedback inhibition. A protein with enhanced specific activity can be searched and obtained, for example, various organisms. Furthermore, a highly-active type of an existing protein may also be obtained by introducing a mutation into the existing protein. The mutation to be introduced may be, for example, substitution, deletion, insertion, or addition of one or several amino acid residues at one or several positions of the protein. The mutation can be introduced by, for example, such a site-specific mutation method as mentioned above. Moreover, introduction of a mutation may be performed, for example, by as mutagenesis treatment. Examples of the mutagenesis treatments include treatment include X-ray irradiation, ultraviolet irradiation, and a treatment with a mutation treatment such as N-methyl-N'-nitro-N-nitrosoguanidine (MNNG), ethylmethanesulfonate (EMS), and methylmethanesulfonate (MMS). Moreover, DNA may be treated directly with hydroxylamine in vitro to induce random mutations. Eenhancement of the specific activity may be used singly or arbitrarily combined for use with the aforementioned method of enhancing gene expression.

The method of transformation is not particularly limited, and conventionally known methods can be used. Methods of transformation of coryneform bacteria include a protoplast method (Gene, 39, 281-286 (1985)), an electroporation method (Bio/Technology, 7, 1067-1070 (1989)), and an electric pulse method (Japanese Patent Laid-Open (Kokai) No. 2-207791).

An increase in the activity of the protein can be confirmed by measuring the activity of the same protein.

An increased activity of the protein can also be confirmed by confirming that the expression of the gene encoding the same protein was increased. The increased expression of the gene can be confirmed by confirming that the transcription amount of the gene was increased, and by confirming that the amount of protein expressed from the gene is increased.

An increase in the amount of transcription of the gene can be confirmed by comparing the amount of mRNA transcribed from the gene with an unmodified strain such as a wild-type strain or a parent strain. Examples of the method of evaluating the amount of mRNA include Northern hybridization, RT-PCR, microarray, RNA-seq., and the like (Sambrook, J., et. al., Molecular Cloning: A Laboratory Manual/Third Edition, Cold Spring Harbor Laboratory Press, Cold Spring Harbor (USA), 2001). The amount of mRNA may be increased, for example, 1.5 fold or more, 2 fold or more, or 3 fold or more over an unmodified strain.

Confirmation of an increase in the amount of protein can be performed by Western blotting using an antibody (Sambrook, J., et al., Molecular Cloning: A Laboratory Manual/Third Edition, Cold Spring Harbor Laboratory Press, Cold Spring Harbor (USA), 2001). The amount of protein may, for example, be increased 1.5 fold or more, 2 fold or more, or 3 fold or more over the unmodified strain.

The aforementioned method of increasing the activity of the protein can be utilized for the activity enhancement of arbitrary proteins and expression enhancement of arbitrary genes.

<1-4> Method of Reducing Activity of Protein

Hereinafter, a method of reducing the activity of a protein will be described.

The expression "activity of a protein is reduced" means that the activity of the protein is reduced as compared with an unmodified strain. The expression "the activity of a protein is reduced" may specifically mean that the activity of the protein per cell is reduced as compared with that of an unmodified strain. As used herein, the term "unmodified strain" refers to a control strain that has not been modified so as to reduce the activity of a target protein. Examples of the unmodified strain include a wild-type strain and a parent strain. Specific examples of the unmodified strain include the type strain of the species of bacteria chosen to be modified. In addition, the unmodified strains specifically include strains exemplified in relation to the description of bacteria. That is, in one aspect, the activity of a protein may be reduced as compared with the corresponding strain (i.e., the corresponding strain of the species to which the bacterium belongs). Moreover, in another embodiment, the activity of a protein may be reduced as compared with the *C. glutamicum* ATCC 13869 strain. Further, in other embodiment, the activity of a protein may be reduced compared to *C. glutamicum* ATCC 13032 strain. Furthermore, in other embodiment, the activity of a protein may be reduced as compared to *C. glutamicum* AJ12036 (FERM BP-734). Moreover, in other embodiment, the activity of a protein may be reduced as compared to *C. glutamicum* YDK010. Incidentally, the phrase "the activity of a protein is reduced" also encompasses the case where the activity of the protein has completely disappeared. The expression "the activity of a protein is reduced" more specifically means that the number of molecules of the protein per cell is reduced as compared to the unmodified strain, and/or the function of the protein per molecule is reduced as compared with those of an unmodified strain. That is, the term "activity" in the case of "the activity of a protein is reduced" is not limited to the catalytic activity of the protein but may refer to the transcription amount (mRNA amount) or translation amount (protein amount) of the gene encoding the protein. The phrase "the number of molecules of the protein per cell is reduced" may refer to an average value of the number of molecules of each protein per cell. Incidentally, "the number of molecules of protein per cell is reduced" includes the case where the same protein is not present at all. In addition, the expression "the function of the protein per molecule is reduced" also includes the case where the function per molecule of the protein has completely disappeared. The degree of the reduction of the activity of the protein is not particularly limited as long as the activity of the protein is reduced as compared with that of an unmodified strain. The activity of a protein may be reduced to, for example, 50% or less, 20% or less, 10% or less, 5% or less, or 0% of that of an unmodified strain.

The modification such that it reduces the activity of a protein can be achieved by, for example, reducing expression of a gene encoding the protein. The phrase "the expression of a gene is reduced" means that the expression of the gene is reduced as compared with an unmodified strain such as a wild-type strain and a parent strain. The phrase "the expression of a gene is reduced" specifically means that the amount of expression of the gene per cell is reduced as compared with that of an unmodified strain. The phrase "the amount of expression of a gene per cell" may refer to an average value of each amount of expression of the gene per cell. The phrase "the expression of a gene is reduced" more specifically may mean that the transcription amount (mRNA amount) of the gene is reduced and/or the translation amount (the amount of protein) of the gene is reduced. The phrase "the expression of a gene is reduced" includes the case where the gene is not expressed at all. Note, however, the phrase "the expression of a gene is reduced" is also referred to as "the expression of a gene is attenuated". The expression of a gene may be reduced to, for example, 50% or less, 20% or less, 10% or less, 5% or less, or 0% of that of an unmodified strain.

The reduction in gene expression may be due to, for example, a reduction in the transcription efficiency, a reduction in the translation efficiency, or a combination thereof. The reduction of the expression of the gene may be performed by, for example, modifying an expression regulatory sequence gene such as a promoter, Shine-Dalgarno (SD) sequence (also referred to as ribosome-binding site (RBS)), and a spacer region between RBS and the start codon of the gene. In the case of modifying an expression regulatory sequence, the expression regulatory sequence can be modified with one or more nucleotides, two nucleotides or more, or three nucleotides or more. For example, the transcription efficiency of a gene can be reduced by, for example, replacing the promoter of the gene on a chromosome with a weaker promoter. The term "weaker promoter" refers to a promoter in which transcription of a gene becomes weaker than that of an inherent wild-type promoter of the gene. Examples of the weaker promoter include inducible promoters. That is, an inducible promoter can function as a weaker promoter under a non-inducing condition (for example, in the absence of the corresponding inducer). In addition, a part or all of an expression regulatory sequence may be deleted. Further, the reduction of gene expression can also be achieved by, for example, manipulating a factor responsible for expression control. The factor responsible for expression control include low molecules (inducers, inhibitors, and the like) responsible for transcription and translation control, proteins (transcription factors and the like), nucleic acids (siRNA and the like) and the like. Moreover, the reduction of gene expression can be achieved by, for example, introducing a mutation that reduces the expression of the gene into the coding region of the gene. For example, gene expression can be reduced by replacing a codon in the coding region of the gene with a synonymous codon that is used less frequently in a host. In addition, for example, the gene expression itself may be reduced due to destruction of a gene as described below.

In addition, the modification reducing the activity of a protein can be achieved by, for example, disrupting a gene encoding the protein. The expression "a gene is disrupted" means that a gene is modified so as not to produce a normally functioning protein. The phrase "a protein that normally functions is not produced" includes cases where no protein is produced at all from the gene, or cases where the gene produces a protein having a reduced or eliminated function (activity or property) per molecule.

Destruction of a gene can be achieved by, for example, deleting the gene on a chromosome. The term "deleting a gene" refers to deleting a partial or entire region of the coding region of the gene. Furthermore, the entire gene including sequences upstream and downstream from the coding region of the gene on a chromosome may be deleted. The sequences upstream and downstream from the coding region of the gene may contain an expression regulatory sequence of the gene. The region to be deleted may be any region such as an N-terminal region (a region encoding the N-terminal side of a protein), an internal region, a C-terminal region (a region encoding the C-terminal side of a protein), and the like as long as the activity of the protein can be reduced. In general, the longer the region to be deleted, the more surely the gene can be inactivated. The region to be deleted may be, for example, a region having a length of 10% or more, 20% or more, 30% or more, 40% or more, 50% or more, 60% or more, 70% or more, 80% or more, 90% or more, or 95% or more, of the total length of the coding region of the gene. Furthermore, it is preferred that reading frames of the sequences upstream and downstream from the region to be deleted are not the same. Inconsistency of reading frames may cause a frameshift downstream of the region to be deleted.

In addition, destruction of a gene may be achieved by, for example, introducing a mutation for an amino acid substitution (missense mutation), a stop codon (nonsense mutation), addition or deletion of one or two nucleotide residues (frameshift mutation), or the like into the coding region of the gene on a chromosome (Journal of Biological Chemistry 272: 8611-8617 (1997), Proceedings of the National Academy of Sciences, USA 95 5511-5515 (1998), Journal of Biological Chemistry 26 116, 20833-20839 (1991)).

Moreover, destruction of the gene can also be achieved by, for example, inserting another nucleotide sequence into a coding region of the gene on a chromosome. Site of the insertion may be in any region of the gene, but the longer the inserted nucleotide sequence, the more surely the gene can be inactivated. Moreover, it is preferred that the reading frames of the sequences upstream and downstream from the insertion site are not the same. Inconsistency of reading frames may cause a frameshift downstream of the region to be deleted. The other nucleotide sequence is not particularly limited as long as a sequence that reduces or eliminates the activity of the encoded protein is chosen, and examples thereof can include a marker gene such as antibiotic resistance genes, and a gene useful for production of an objective substance.

Particularly, destruction of a gene may be carried out so that the amino acid sequence of the encoded protein is deleted. In other words, the modification for reducing the activity of a protein can be attained by, for example, deleting the amino acid sequence of the protein (a partial or the entire region of the amino acid sequence), specifically, modifying a gene so as to encode a protein of which the amino acid sequence (a partial or the entire region of the amino acid sequence) is deleted. The term "deletion of the amino acid sequence of a protein" can refer to deletion of a partial or entire region of the amino acid sequence of the protein. In addition, the term "deletion of the amino acid sequence of a protein" can mean that the original amino acid sequence disappears in the protein, and also can include cases where the original amino acid sequence is changed to another amino acid sequence. That is, for example, a region that was changed to another amino acid sequence by frameshift may be regarded as a deleted region. When the amino acid sequence of a protein is deleted, the total length of the protein is typically shortened, but there can also be cases where the total length of the protein is not changed or is extended. For example, by deletion of a partial or entire region of the coding region of a gene, a region encoded by the deleted region can be deleted in the amino acid sequence of the encoded protein. In addition, for example, by introduction of a stop codon into the coding region of a gene, a region encoded by the downstream region of the introduction site can be deleted in the amino acid sequence of the encoded protein. In addition, for example, by frameshift in the coding region of a gene, a region encoded by the frameshift region can be deleted. The aforementioned descriptions concerning the position and length of the region to be deleted in deletion of a gene can be similarly applied to the position and length of the region to be deleted in deletion of the amino acid sequence of a protein.

Such modification of a gene on a chromosome as described above can be attained by, for example, preparing a destruction-type gene modified so that it is unable to produce a protein that normally functions, and transforming a host with a recombinant DNA containing the destruction-type gene to cause homologous recombination between the destruction-type gene and the wild-type gene on a chromosome and thereby substitute the destruction-type gene for the wild-type gene on the chromosome. In this procedure, if a marker gene selected according to the characteristics of the host such as auxotrophy is included in the recombinant DNA, the operation becomes easier. Examples of the destruction-type gene can include a gene of which a partial or entire region of the coding region is deleted, gene including a missense mutation, gene including a nonsense mutation, gene including a frame shift mutation, and gene introduced with an insertion sequence such as a transposon or marker gene. The protein encoded by the destruction-type gene has a conformation different from that of the wild-type protein, even if it is produced, and thus the function thereof is reduced or eliminated. The structure of the recombinant DNA used for homologous recombination is not particularly limited as long as homologous recombination occurs in the desired manner. For example, a host is transformed with a linear DNA containing a destruction-type gene and having sequences upstream and downstream of a wild-type gene on a chromosome at both ends thereof to cause homologous recombination upstream and downstream of the-wild type gene, respectively, thereby enabling substitution of the wild-type gene with the destruction-type gene. Such gene destruction based on gene substitution utilizing homologous recombination has already been established, and includes methods using a linear DNA such as a method called "Red-driven integration" (Datsenko, K A, and Wanner, B. L Proc. Natl. Acad. Sci. USA. 97: 6640-6645 (2000), and a combined method (see WO 2005/010175) of a Red driven integration method with an excision system derived from λ phage (Cho, E. H., Gumport, R. I, Gardner, J. F. J. Bacteriol. 184: 5200-5203 (2002)), a method of using a plasmid containing a temperature-sensitive replication origin, a method using a plasmid capable of conjugative transfer, a method using a suicide vector which does not have an origin of replication which functions in a host (U.S. Pat. No. 6,303,383, Japanese Patent Laid-open (Kokai) No. 05-007491), and the like. Note, however, the method of modifying a chromosome utilizing such homologous recombination is not limited to destruction of a target gene, but can be used for arbitrary modifications of chromosomes, such as modification of an expression regulatory sequence.

In addition, the modification such that it reduces the activity of a protein may be performed, for example, by a mutagenesis treatment. Examples of the mutagenesis treatment include X-ray irradiation, ultraviolet irradiation and treatment with a mutation agent such as N-methyl-N'-nitro-N-nitrosoguanidine (MNNG), ethyl methane sulfonate (EMS), and methyl methane sulfonate (MMS).

When a protein functions as a complex consisting of a plurality of subunits, all of the subunits may be modified or only a portion may be modified as long as the activity of the protein is eventually reduced. That is, for example, all of the genes encoding the subunits may be disrupted, or only some may be disrupted. In addition, when a plurality of isozymes is present in a protein, all activities of a plurality of isozymes may be reduced or only a partial activity may be reduced as long as the activity of the protein is consequently reduced. That is, for example, all of the genes encoding the isozymes may be disrupted or the like, or only some may be disrupted or the like.

The methods of reducing the activity of proteins described above may be used singly or arbitrarily combined for use.

A reduction in the activity of a protein can be confirmed by measuring the activity of the protein.

A reduction in the activity of a protein can also be confirmed by confirming that the expression of a gene encoding the protein is reduced. A reduction in the expression of a gene can be confirmed by confirming that the amount of transcription of the gene has been reduced, or by confirming that the amount of the protein expressed from the gene has been reduced.

A reduction in the amount of transcription of a gene can be confirmed by comparing the amount of mRNA transcribed from the gene with that of an unmodified strain. Examples of the method of evaluating the amount of mRNA include Northern hybridization, RT-PCR, microarray, RNA-seq, and the like (Sambrook, J., et al., Molecular Cloning: A Laboratory Manual/Third Edition, Cold Spring Harbor Laboratory Press, Cold Spring Harbor (USA), 2001)). The amount of mRNA may be reduced to, for example, 50% or less, 20% or less, 10% or less, 5% or less, or 0% of that of an unmodified strain.

A reduction in the amount of protein can be confirmed by Western blotting using antibodies (Sambrook, J., et al., Molecular Cloning: A Laboratory Manual/Third Edition, Cold Spring Harbor Laboratory Press, Cold Spring Harbor (USA), 2001). The amount of protein may be reduced to, for example, 50% or less, 20% or less, 10% or less, 5% or less, or 0% of that of an unmodified strain.

Destruction of a gene can be confirmed by determining the nucleotide sequence of a part or the entire gene, restriction enzyme map, full length, or the like according to the means used for the destruction.

The aforementioned method of reducing the activity of a protein can be applied to reduction in the activity of arbitrary proteins or the expression of arbitrary genes.

<2> Method of Producing L-Amino Acid

Described herein is a method of producing an L-amino acid by cultivating the bacterium in a culture medium and accumulating an L-amino acid in the culture medium and/or in bacterial cells; and collecting the L-amino acid from the culture medium and/or the bacterial cells. The L-amino acid is as described above. A single type of L-amino acid may be produced, two or more L-amino acids may be produced.

The chosen culture medium is not particularly limited as long as the bacterium can proliferate and produce a target L-amino acid. As a culture medium, for example, a common culture medium used for culture of bacteria such as coryneform bacteria can be used. As the culture medium, for example, a culture medium containing components such as a carbon source, nitrogen source, phosphoric acid source, sulfur source, other various organic components, and inorganic components as necessary. Types and concentrations of the culture medium components may be appropriately set according to various conditions such as the type of bacteria used.

Specific examples of the carbon source include saccharides such as glucose, fructose, sucrose, lactose, galactose, xylose, arabinose, blackstrap molasses, hydrolysates of starches, and hydrolysates of biomass, organic acids such as acetic acid, fumaric acid, citric acid, and succinic acid, alcohols such as glycerol, crude glycerol, and ethanol, fatty acids. The carbon sources particularly include saccharides. The carbon sources more particularly include glucose and fructose. Saccharides such as glucose and fructose may be used singly or in combination with other carbon sources, as carbon sources. For example, saccharide with fructose as a constituent saccharide may be used as a carbon source. Saccharides with fructose as a constituent saccharide include fructose, sucrose, and fructooligosaccharides. The saccharides with fructose as a constituent saccharide may be used singly or in combination with other carbon sources, as a carbon source. Raw materials derived from plants may be suitably used as carbon sources. Examples of the plant include corn, rice, wheat, soybean, sugarcane, beet and cotton. Examples of the raw materials derived from plants include organs such as root, stem, trunk, branch, leaf, flower, and seed, plants containing them, and decomposition products of those plant organs. The form of the raw materials derived from plants is not particularly limited, and any form of raw material, for example, unprocessed commodities, juice, ground product, purified product and the like can be used. In addition, five-carbon saccharides such as xylose, and six-carbon saccharides such as glucose, or a mixture thereof can be used by being obtained from, for example, plant biomass. Specifically, these saccharides can be obtained by subjecting plant biomass to treatment such as steam treatment, concentrated acid hydrolysis, dilute acid hydrolysis, hydrolysis with an enzyme such as cellulase, alkali treatment and the like. Since hemicellulose is generally more easily hydrolyzed than cellulose, it is possible to hydrolyze hemicellulose in plant biomass in advance to release 5-carbon saccharide and then hydrolyze cellulose to form 6-carbon saccharide. In addition, xylose may be supplied, for example, by conversion from 6-carbon saccharide by allowing the bacterium to possess a conversion route from 6-carbon saccharide such as glucose to xylose. As carbon sources, a single type carbon source may be used, or two or more carbon sources may be used in combination.

Specific examples of the nitrogen source include ammonium salts such as ammonium sulfate, ammonium chloride and ammonium phosphate, organic nitrogen sources such as peptone, yeast extract, meat extract and soybean protein decomposition products, ammonia and urea. Ammonia gas or aqueous ammonia used for pH adjustment may be used as the nitrogen source. As the nitrogen source, a single type of nitrogen source may be used, or two or more types of nitrogen sources may be combined for use.

Specific examples of the phosphoric acid source include phosphates such as potassium dihydrogen phosphate and dipotassium hydrogen phosphate, and phosphoric acid polymers such as pyrophosphoric acid. As the phosphoric acid source, a single type of phosphoric acid source may be used, and two or more types of phosphoric acid sources may be combined for use.

Specific examples of the sulfur source include inorganic sulfur compounds such as sulfates, thiosulfates and sulfites, and sulfur-containing amino acids such as cysteine, cystine and glutathione. As the sulfur source, a single type of sulfur source may be used, and two or more types of sulfur sources may be combined for use.

Specific examples of various other organic components and inorganic components include inorganic salts such as sodium chloride and potassium chloride; trace metals such as iron, manganese, magnesium and calcium; vitamins such as vitamin B1, vitamin B2, vitamin B6, nicotine acid, nicotinic acid amide, and vitamin B12; amino acids; nucleic acids; and organic components containing those such as peptone, casamino acids, yeast extract, and soybean protein decomposition products. Various other organic components and inorganic components can be used singly, or two or more thereof may be combined for use.

Moreover, when using an auxotrophic mutant that requires an amino acid and the like for growth thereof, it is preferable to supply a required nutrient to a culture medium.

It is also preferable to restrict the amount of biotin in a culture medium, or to add a surfactant or penicillin to the culture medium.

The culture conditions are not particularly limited as long as the bacterium can proliferate and produce a target L-amino acid. The culture can be performed, for example, under typical conditions used for culturing bacteria such as coryneform bacteria. The culture conditions may be appropriately set according to various conditions such as the type of chosen bacterium.

The culture can be performed using a liquid culture medium. Upon culture, a culture medium of the bacterium cultured on a solid culture medium such as agar culture medium may be directly inoculated into a liquid culture medium, or the bacterium cultured in a liquid culture medium as seed culture may be inoculated into a liquid culture medium for the main culture. That is, the culture may be performed separately in the seed culture and the main culture. In such a case, the culture conditions of the seed culture and the main culture may or may not be the same. The amount of the bacterium present in the culture medium at the time of the start of the culture is not particularly limited. The main culture may be performed, for example, by inoculating a 1 to 50% (v/v) seed culture solution into the culture medium of the main culture.

The culture can be performed by batch culture, Fed-batch culture, continuous culture, or combinations thereof. It is noted that the culture medium used at the time of the start of the culture is also referred to as "starting culture medium". In addition, a culture medium supplied to a culture system (fermentation tank) in Fed-batch culture or continuous culture is also referred to as "feed culture medium." Furthermore, supplying a feed culture medium to a culture system in Fed-batch culture or continuous culture is also referred to as "feed". Incidentally, when the culture is performed separately as seed culture and main culture, for example, both the seed culture and the main culture may be performed as batch culture. Moreover, for example, the seed culture may be performed by batch culture, and the main culture may be performed by Fed-batch culture or continuous culture.

Each culture medium component may be present in the starting culture medium, a feed culture medium, or both. The type of component present in the starting culture medium may or may not be the same as the type of components present in the feed culture medium. In addition, the concentration of each component present in the starting culture medium may or may not be the same as the concentration of each component contained in the feed culture medium. Furthermore, two or more types of feed culture media containing different types and/or different concentrations of components may be used. For example, when the culture medium is intermittently fed for a plurality of times, the types and/or concentrations of components in the feed culture media may or may not be the same for each feeding.

The concentration of the carbon source in the culture medium is not particularly limited as long as the bacterium can proliferate and produce an L-amino acid. The concentration of the carbon source in the culture medium may be as high as possible, for example, as long as the production of L-amino acid is not prevented. The concentration of the carbon source in the culture medium may be, for example, 1 to 30 w/v %, 3 to 10 w/v %, as the initial concentration (concentration in the starting culture medium). In addition, the carbon source may be additionally supplied to the culture medium as required. For example, the additional carbon source may be supplied to the culture medium depending on the consumption of the carbon source accompanying progress of the fermentation.

Culture can be performed, for example, under aerobic conditions. The aerobic condition refers to a condition that the concentration of dissolved oxygen in a liquid culture medium is 0.33 ppm or more, which is the detection limit for the detection with an oxygen membrane electrode, and can be 1.5 ppm or more. The oxygen concentration can be controlled to, for example, about 5 to 50% or about 10%, relative to the saturated oxygen concentration. Specifically, the culture under aerobic conditions can be performed by aeration culture, shake culture, spinner culture, or a combination thereof. The pH of the culture medium may be, for example, pH 3 to 10 or pH 4.0 to 9.5. During the culture, the pH of the culture medium can be adjusted as required. The pH of the culture medium can be adjusted by using various alkaline or acidic substances such as ammonia gas, ammonia water, sodium carbonate, sodium bicarbonate, potassium carbonate, potassium bicarbonate, magnesium carbonate, sodium hydroxide, potassium hydroxide, calcium hydroxide and magnesium hydroxide. The culture temperature may be, for example, 20 to 40° C. or 25 to 37° C. The culture period may be, for example, 10 hours to 120 hours. The culture may be continued, for example, until a carbon source in the culture medium is consumed or the activity of the bacterium is lost. By culturing the bacterium under such conditions, an L-amino acid accumulates in the culture medium and/or in the bacterial cells.

Moreover, when an L-glutamic acid is produced, it can also be cultured, while allowing an L-glutamic acid to precipitate in a culture medium by using the liquid culture medium adjusted to the conditions of precipitation of an L-glutamic acid. The conditions of precipitation of L-glutamic acid include, for example, a pH of 5.0 to 4.0, a pH of 4.5 to 4.0, a pH of 4.3 to 4.0, or a pH of 4.0 (EP 1078989A). Moreover, use of the liquid culture medium adjusted to the conditions of precipitation of L-glutamic acid enables more efficient crystallization by adding pantothenic acid to the culture medium (WO 2004/111258). Moreover, use of the liquid culture medium adjusted to the conditions of precipitation of L-glutamic acid enables more efficient crystallization by adding seed crystals of L-glutamic acid to the culture medium (EP1233069A). Furthermore, use of the liquid culture medium adjusted to the conditions for precipitation of L-glutamic acid enables more efficient crystallization by adding crystals of L-glutamic acid and L-lysine to the culture medium as seed crystals (EP1624069A).

When a basic amino acid is produced, the culture step (fermentation step) may be conducted so that bicarbonate ions and/or carbonate ions are the counter ions of the basic amino acid. Such a form of fermentation is also referred to as "carbonate fermentation." The carbonate fermentation allows for the fermentation and production of the basic amino acid while reducing the amount used of sulfate and/or chloride ions, which are conventionally used as counter ions for basic amino acids. Carbonate fermentation can be performed as described, for example, in US2002-025564A, EP1813677A, and Japanese Patent-Laid Open (Kokai) No. 2002-65287.

The fermentation liquid can be treated, for example, in a liquid cyclone. The liquid cyclone, which is, for example, made of ceramic, stainless steel, or resin with a general shape and a diameter of a cylindrical portion of 10 to 110 mm, can be used. The feed volume of the fermentation liquid into the liquid cyclone can be set, for example, according to a bacterial cell concentration and an L-amino acid concentration in the fermentation liquid. The feed rate of the fermentation liquid to the liquid cyclone may be, for example, 2 to 1200 L/min.

Production of an L-amino acid can be confirmed by publicly known methods used for detection or identification of compounds. Such methods include, for example, HPLC, LC/MS, GC/MS, and NMR. These methods can be used singly or appropriately combined for use.

L-amino acids can be collected from the fermentation liquid by publicly known methods used for separation and purification of compounds. Such methods include, for example, an ion exchange resin method (Nagai, H. et al., Separation Science and Technology, 39(16), 3691-3710), a precipitation method, a membrane separation method (Japanese Patent-Laid Open (Kokai) No. 9-164323 and Japanese Patent-Laid Open (Kokai) No. 9-173792), a crystallization method (WO 2008/078448, WO 2008/078646). These methods may be used singly or appropriately combined for use. Note, however, when an L-amino acid accumulates in bacteria cells, for example, the L-amino acid can be recovered from the supernatant obtained by crushing the bacteria cells by ultrasonic or the like and removing the bacteria cells by centrifugation, using an ion exchange resin method or the like. The collected L-amino acid may be a free form thereof, salts thereof, or mixtures thereof. Examples of the salts include sulfate, hydrochloride, carbonate, ammonium salts, sodium salts, and potassium salts. In the case of producing an L-glutamic acid, the collected L-glutamic acid may be, for example, a free L-glutamic acid, sodium L-glutamate (for example, monosodium L-glutamate; MSG), ammonium L-glutamate (for example, monoammonium L-glutamate) or mixtures thereof. For example, monoammonium L-glutamate (MSG) is obtained by crystallizing ammonium L-glutamate in fermentation liquid with acid and adding an equimolar amount of sodium hydroxide to the crystals. Activated carbon may be added to decolorize a sample before and after crystallization (see, for example, Tetsuya KAWAKITA, "Industrial Crystallization for Monosodium L-Glutamate.", Bulletin of the Society of Sea Water Science, Japan, Vol. 56:5). The monosodium L-glutamate crystals can be used, for example, as an umami seasoning. The monosodium L-glutamate crystals may be used as a seasoning by mixing with a nucleic acid such as sodium guanylate and sodium inosinate, which also have umami taste.

When an L-amino acid precipitates in the culture medium, it can be collected by centrifugation, filtration, or the like. Moreover, the L-amino acid precipitated in the culture medium may also be isolated together with the L-amino acid dissolved in the culture medium, after the L-amino acid dissolved in the culture medium is crystallized.

Incidentally, the collected L-amino acid may also contain other components such as bacterial cells, culture media components, moisture, and bacterial metabolic by-products, in addition to the L-amino acid. The collected L-amino acid may be purified at a desired extent. Purity of the collected L-amino acid may be, for example, 50% (w/w) or higher, 85% (w/w) or higher, or 95% (w/w) or higher (Japanese Patent 1214636, U.S. Pat. Nos. 5,431,933, 4,956,471, 4,777, 051, 4,946,654, 5,840,358, 6,238,714, US2005/0025878).

EXAMPLES

The present invention will be more specifically described below with reference to non-limiting examples.
<1> Construction of Modified Strain of *Corynebacterium Glutamicum*
<1-1> Construction of Vector for aspT Gene Deletion
By using a chromosome DNA of *C. glutamicum* ATCC 13869 as a template, a DNA fragment of about 1 kbp upstream on the 5' side of aspT gene (CGBL 0102840) encoding aspartate transaminase and a DNA fragment of about 1 kbp downstream on the 3' side thereof, respectively, are amplified by PCR using appropriately designed primers. The amplified DNA fragments are inserted into the SmaI site of pBS5T (WO 2006/057450) by an infusion reaction to obtain a vector for aspT gene deletion.
<1-2> Construction of Vector for malE Gene Deletion
By using a chromosome DNA of *C. glutamicum* ATCC 13869 as a template, a DNA fragment of about 1 kbp upstream on the 5' side of malE gene (CGBL 0129850) encoding a malic enzyme and a DNA fragment of about 1 kbp downstream on the 3' side thereof, respectively, are amplified by PCR using appropriately designed primers. The amplified DNA fragments are inserted into the SmaI site of pBS5T (WO 2006/057450) by an infusion reaction to obtain a vector for malE gene deletion.
<1-3> Construction of Vector for poxB Gene Deletion
By using a chromosome DNA of *C. glutamicum* ATCC 13869 as a template, a DNA fragment of about 1 kbp upstream on the 5' side of poxB gene (CGBL 0125410) encoding pyruvate dehydrogenase and a DNA fragment of about 1 kbp downstream on the 3' side thereof, respectively, is amplified by PCR using appropriately designed primers. The amplified DNA fragments are inserted into a SmaI site of pBS5T (WO 2006/057450) by an infusion reaction to obtain a vector for poxB gene deletion.
<1-4> Construction of Expression Vector of Ack Gene
Using a chromosome DNA of *C. glutamicum* ATCC 13869 as a template, a DNA fragment containing ack gene (CGBL_0126910) encoding acetate kinase, was amplified by PCR using primers of SEQ ID NOs: 19 and 20. The amplified DNA fragment and pVK9 (US2006-0141588) cut with bamHI and pstI were linked by an infusion reaction to obtain an expression vector pVK9-Plac ackA for ack gene.

By using a chromosome DNA of *C. glutamicum* ATCC 13869 as a template, a DNA fragment containing an upstream sequence of msrA gene derived from *C. glutamicum* (including the promoter region, 369 bp), was amplified by PCR using primers of SEQ ID NOs: 21 and 22. Separately, by using a chromosome DNA of *C. glutamicum* ATCC 13869 as a template, a DNA fragment containing ack gene (CGBL_0126910) was amplified by PCR using primers of SEQ ID NOs: 23 and 20. Both amplified DNA fragments and pVK9 (US2006-0141588) cut with bamHI and pstI were linked by an infusion reaction to obtain an expression vector pVK9-PmsrA ackA for the ack gene.

<1-5> Construction of Expression Vector of glpX Gene

By using a chromosomal DNA of *E. coli* K-12 MG1655 (ATCC 47076) as a template, a DNA fragment containing glpX gene encoding fructose-1,6-bisphosphatase, was amplified by PCR using primers of SEQ ID NOs: 24 and 25. The amplified DNA fragment and pVK9 (US2006-0141588) cut with bamHI and pstI were linked by an infusion reaction to obtain an expression vector pVK9-Plac glpX for glpX gene.

<1-6> Construction of Modified Strains of *Corynebacterium Glutamicum*

A *C. glutamicum* 2256ΔsucAΔldhA yggB* strain (WO 2014/185430) is transformed with each constructed vector for gene deletion. By using the resulting transformants, strains are selected according to the method described in WO 2006/057450 to obtain an aspT gene-deficient strain, a malE gene-deficient strain, and a poxB gene-deficient strain.

A strain with enhanced expression of the ack gene was obtained by introducing the constructed expression vector of ackA gene, pVK9-Plac ackA or pVK9-PmsrA ackA singly or in combination with pVS7-xfp (US2018-0282773) to a *C. glutamicum* 2256ΔsucAΔldhA yggB* strain (WO 2014/185430). pVS7-xfp is an expression vector of phosphoketolase gene (xfp) derived from *B. longum* JCM1217 (US2018-0282773).

The constructed expression vectors of glpX gene, pVK9-Plac glpX and pVS7-xfp (US2018-0282773) were introduced into a *C. glutamicum* 2256ΔsucAΔldhA yggB* strain (WO 2014/185430) to obtain a strain with enhanced expression of glpX gene.

pVK9 was introduced into a *C. glutamicum* 2256ΔsucAΔldhA yggB* strain (WO 2014/185430) singly or in combination with pVS7-xfp (US2018-0282773) to obtain a control strain.

The *C. glutamicum* 2256ΔsucAΔldhA yggB* strain is an L-glutamic acid producing-strain derived from a *C. glutamicum* 2256 (ATCC 13869), lacking ldhA and sucA genes and containing an IS mutation (V419::IS) in yggB gene. The nucleotide sequence of the mutant yggB gene (V419::IS) and the amino acid sequence of the mutant YggB protein (V419::IS) encoded by the gene are shown of SEQ ID NOs: 17 and 18, respectively.

<2> L-Glutamic Acid Production Culture

L-glutamic acid production culture was performed using each of the constructed strains (i.e., the control strain and the strain with enhanced expression of its ack gene and the strain with enhanced expression of glpX gene). The composition of the media used is shown in Table 1. A culture medium in which a carbon source is Glucose is also referred to as "Glc culture medium" and a culture medium in which a carbon source is Fructose is also referred to as "Frc culture medium."

TABLE 1

| Culture medium composition | |
| --- | --- |
| Glucose or Fructose | 80 g/L |
| $(NH_4)_2SO_4$ | 30 g/L |
| $KH_2PO_4$ | 1 g/L |
| $MgSO_4 \cdot 7H_2O$ | 0.4 g/L |
| $FeSO_4 \cdot 7H_2O$ | 0.01 g/L |
| $MnSO_4 \cdot 5H_2O$ | 0.01 g/L |
| $VB_1$ | 200 μg/L |
| Biotin | 300 μg/L |
| Mameno | 0.48 g/L |
| $CaCO_3$ | 50 g/L |
| Succinic acid | 1 g/L |

A culture medium with the above composition adjusted to pH 8.0 with KOH was prepared and sterilized by using an autoclave (115° C., 10 min). The sterilized culture medium was supplemented with calcium carbonate sterilized by dry heating (180° C., 6 hr) to a final concentration of 50 g/L and used for the culture.

Each strain was inoculated into 5 mL of the above culture medium (containing g/L calcium carbonate) staked in a thick test tube and subjected to shaking culture at 120 rpm in a box shaker (ABLE ML-190) at 31.5° C. Culture liquid was sampled 25 or 30 hours after the start of the culture. The concentration of L-glutamic acid in the culture liquid was determined by using a Biotech Analyzer AS-310 (manufactured by Sakura S.I.), and the yield per sugar of L-glutamic acid was calculated.

Figure 2:
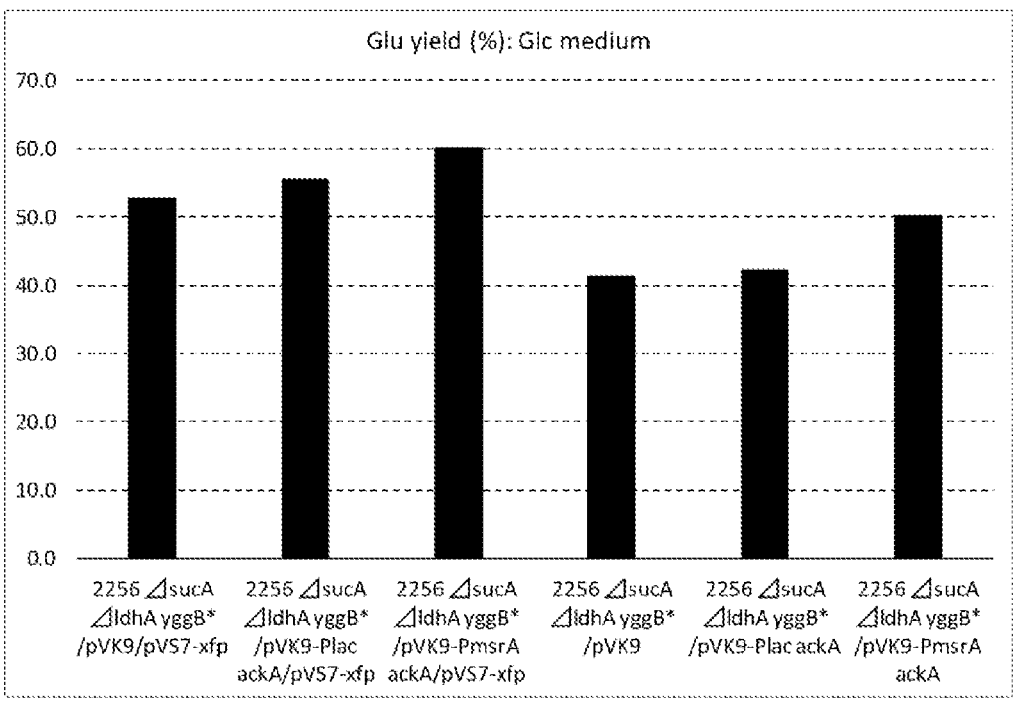
FIG. 2 shows yield per sugar of L-glutamic acid in a control strain and a strain with enhanced expression of ack gene when glucose is used as a carbon source.
Figure 3:
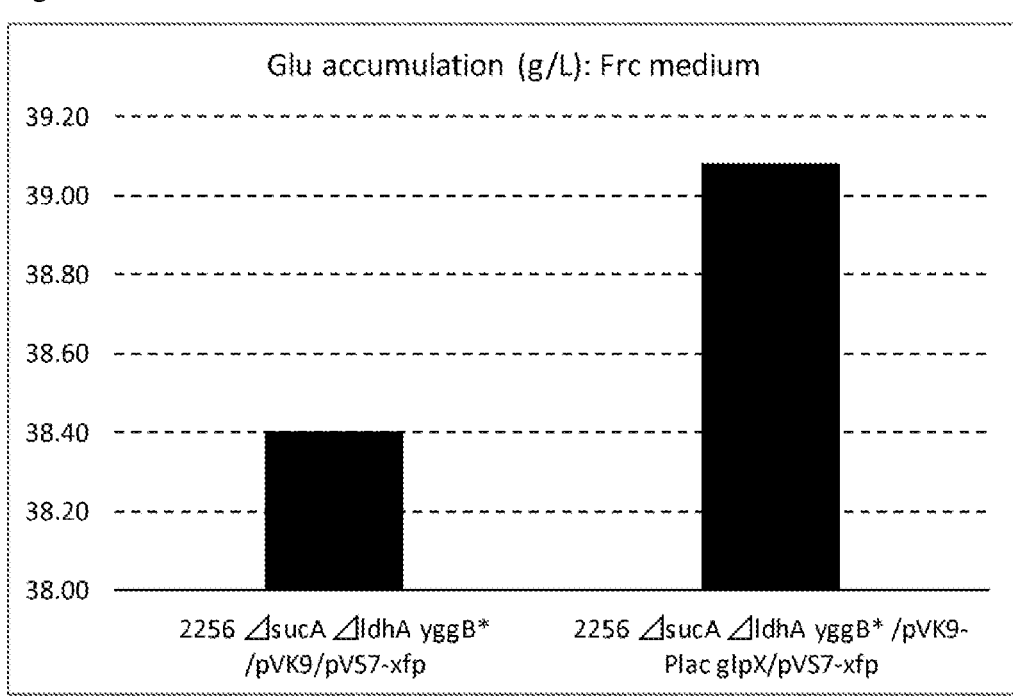
FIG. 3 shows the amount of L-glutamic acid accumulated in a control strain and a strain with enhanced expression of glpX gene when fructose is used as a carbon source.
Figure 4:
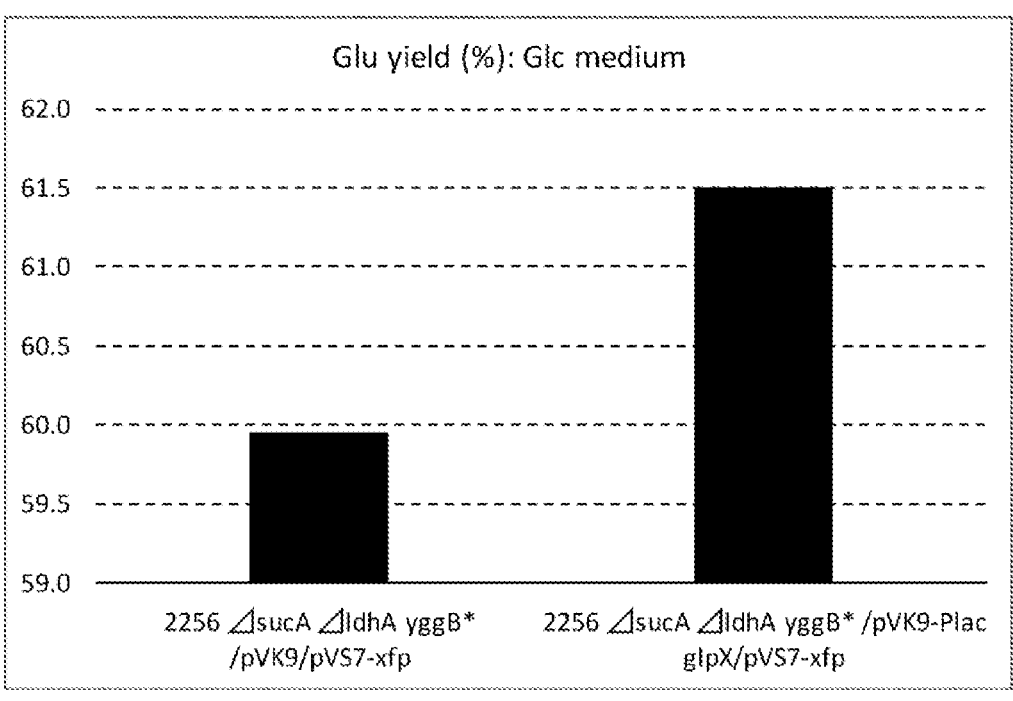
FIG. 4 shows a yield per sugar of L-glutamic acid in a control strain and a strain with enhanced expression of glpX gene when glucose is used as a carbon source.

The results are shown in FIGS. 1 to 4. In a case in which strains with enhanced expression of ack gene (2256ΔsucAΔldhA yggB*/pVK9-Plac ackA/pVS7-xfp, 2256ΔsucAΔldhA yggB*/pVK9-PmsrA ackA/pVS7-xfp, 2256ΔsucAΔldhA yggB*/pVK9-Plac ackA, and 2256ΔsucAΔldhA yggB*/pVK9-PmsrA ackA), used glucose as carbon sources, they exhibited the higher amount of L-glutamic acid accumulated and the higher yield per sugar of L-glutamic acid than the corresponding control strains (2256 Δ sucA Δ ldhA yggB*/pVK9/pVS7-xfp for 2256 Δ sucA Δ ldhA yggB*/pVK9-Plac ackA/pVS7-xfp and 2256 Δ sucA Δ ldhA yggB*/pVK9-PmsrA ackA/pVS7-xfp; and 2256 Δ sucA Δ ldhA yggB*/pVK9 for 2256 Δ sucA Δ ldhA yggB*/pVK9-Plac ackA and 2256 Δ sucA ΔldhA yggB*/pVK9-PmsrA ackA, respectively (FIGS. 1 and 2). In addition, the strain with enhanced expression of glpX gene (2256 Δ sucA Δ ldhA yggB*/pVK9-Plac glpX/pVS7-xfp) exhibited the higher amount of L-glutamic acid accumulated (FIG. 3) than the corresponding control strain (2256 Δ sucA Δ ldhA yggB*/pVK9/pVS7-xfp) when fructose was used as a carbon source, and it exhibited the higher yield per sugar of L-glutamic acid than the corresponding control strain (2256 Δ sucA Δ ldhA yggB*/pVK9/pVS7-xfp) when glucose was used as a carbon source, (FIG. 4).

Moreover, L-glutamic acid production culture of an aspT gene-deficient strain, a malE gene-deficient strain, and a poxB gene-deficient strain are performed in the same procedure, thereby confirming improvements in L-glutamic acid production.

INDUSTRIAL AVAILABILITY

According to the present invention, the L-amino acid-producing ability of a coryneform bacterium can be improved and an L-amino acid can be efficiently produced.

Description of Sequence Listing

SEQ ID NO: 1: Nucleotide sequence of aspT gene of *Corynebacterium glutamicum* 2256 (ATCC 13869)

SEQ ID NO: 2: Amino acid sequence of AspT protein of *Corynebacterium glutamicum* 2256 (ATCC 13869)

SEQ ID NO: 3: Nucleotide sequence of malE gene of *Corynebacterium glutamicum* 2256 (ATCC 13869)

SEQ ID NO: 4: Amino acid sequence of malE protein of *Corynebacterium glutamicum* 2256 (ATCC 13869)

SEQ ID NO: 5: Nucleotide sequence of poxB gene of *Corynebacterium glutamicum* 2256 (ATCC 13869)

SEQ ID NO: 6: Amino acid sequence of PoxB protein of *Corynebacterium glutamicum* 2256 (ATCC 13869)

SEQ ID NO: 7: Nucleotide sequence of ack gene of *Corynebacterium glutamicum* 2256 (ATCC 13869)

SEQ ID NO: 8: Amino acid sequence of ack protein of *Corynebacterium glutamicum* 2256 (ATCC 13869)

SEQ ID NO: 9: Nucleotide sequence of ack gene of *Escherichia coli* K-12 MG1655

SEQ ID NO: 10: Amino acid sequence of ack protein of *Escherichia coli* K-12 MG1655

SEQ ID NO: 11: Nucleotide sequence of glpX gene of *Corynebacterium glutamicum* ATCC 13032

SEQ ID NO: 12: Amino acid sequence of glpX protein of *Corynebacterium glutamicum* ATCC 13032

SEQ ID NO: 13: Nucleotide sequence of glpX gene of *Escherichia coli* K-12 MG1655

SEQ ID NO: 14: Amino acid sequence of GlpX protein of *Escherichia coli* K-12 MG1655

SEQ ID NO: 15: Nucleotide sequence of yggB gene of *Corynebacterium glutamicum* 2256 (ATCC 13869)

SEQ ID NO: 16: Amino acid sequence of yggB protein of *Corynebacterium glutamicum* 2256 (ATCC 13869)

SEQ ID NO:17: Nucleotide sequence of mutant yggB gene (V419::IS) of *Corynebacterium glutamicum* 2256 (ATCC 13869)

SEQ ID NO: 18: Amino acid sequence of mutant yggB protein (V419::IS) of *Corynebacterium glutamicum* 2256 (ATCC 13869)

SEQ ID NOs: 19 to 25: Primers

---

The invention claimed is:

1. A method of producing an L-amino acid, comprising:

cultivating a coryneform bacterium having L-amino acid-producing ability in a culture medium to accumulate an L-amino acid in the culture medium and/or in cells of the bacterium; and collecting the L-amino acid from the culture medium and/or the cells;

wherein the L-amino acid is L-glutamic acid family, and wherein the bacterium has a modification for increasing activity of acetate kinase, and optionally an additional a modification for increasing activity of fructose-1,6-bisphosphatase, combinations thereof;

wherein expression of the gene encoding acetate kinase is increased by increasing the copy number of the gene and/or by modifying an expression regulatory sequence of the gene;

wherein the acetate kinase is selected from the group consisting of:

(i) a protein comprising the amino acid sequence of SEQ ID NO: 8 or 10, (ii) a protein comprising the amino acid sequence of SEQ ID NO: 8 or 10 except that said amino acid sequence includes substitution, deletion, insertion, and/or addition of 1 to 10 amino acid residues, and has acetate kinase activity, and (iii) a protein comprising an amino acid sequence having 90% or more identity to the amino acid sequence of SEQ ID NO: 8 or 10, and has acetate kinase activity;

wherein the fructose-1,6-bisphosphatase is selected from the group consisting of:

(i) a protein comprising the amino acid sequence of SEQ ID NO: 12 or 14, (ii) a protein comprising the amino acid sequence of SEQ ID NO: 12 or 14 except that said amino acid sequence includes substitution, deletion, insertion, and/or addition of 1 to 10 amino acid residues, and has fructose-1,6-bisphosphatase activity, and (iii) a protein comprising an amino acid sequence having 90% or more identity to the amino acid sequence of SEQ ID NO: 12 or 14, and has fructose-1,6-bisphosphatase activity;

wherein the bacterium has been further modified so that the activity of phosphoketolase is increased as compared to an unmodified bacterium; and wherein the bacterium is of the genus *Corynebacterium*.

2. The method according to claim 1, wherein the activity of the acetate kinase is increased by increasing expression of a gene encoding acetate kinase, and wherein the activity of the fructose-1,6-bisphosphatase is increased by increasing expression of a gene encoding fructose-1,6-bisphosphatase.

3. The method according to claim 2, wherein expression of the gene encoding fructose-1,6-bisphosphatase is increased by increasing the copy number of the gene and/or by modifying an expression regulatory sequence of the gene.

4. The method according to claim 1, wherein the phosphoketolase is D-xylulose-5-phosphate phosphoketolase and/or fructose 6-phosphate phosphoketolase.

5. The method according to claim 1, wherein the bacterium is *Corynebacterium glutamicum*.

6. The method according to claim 1, wherein the L-glutamic acid is ammonium L-glutamate or sodium L-glutamate.

* * * * *

```
                            SEQUENCE LISTING

Sequence total quantity: 25
SEQ ID NO: 1              moltype = DNA  length = 1281
FEATURE                  Location/Qualifiers
source                   1..1281
                         mol_type = genomic DNA
                         organism = Corynebacterium glutamicum
SEQUENCE: 1
atgagttcag tttcgctgca ggattttgat gcagagcgaa ttggtctgtt ccacgaggac    60
attaaacgca agtttgatga gctcaagtca aaaaatctga agctggatct tactcgcggt   120
aagccttcgt cggagcagtt ggatttcgct gatgagctgt tggcgttgcc tggtaagggc   180
gatttcaagg ctgcggatgg tactgatgtc cgtaactatg gcgggctgga tggcattgtt   240
gatattcgtc agatttgggc ggatttgctg ggtgttcctg tggagcaggt gctggcgggg   300
gatgcttcga gcttgaacat catgtttgat gtgatcagct ggtcgtacac ttttggtaac   360
aatgattcgg ttcagccttg gtcgaaggaa gaaactgtta agtggatttg tcctgttccg   420
ggatatgatc gccatttctc catcacggag cgtttcggct ttgagatgat ttctgtgcca   480
atgaatgaag acggccctga tatggatgct gttgaggaat tggtcaagga tccgcaggtt   540
aagggcatgt gggttgtgcc ggtattttct aacccgactg gtttcacggt gtcggaggac   600
gtcgcaaagc gtctgagcac gatggaaact gcggcgccgg acttccgcgt ggtgtgggat   660
aacgcttacg ccgttcatac tctgaccgat gagttccctg aggtcatcga catcgttggg   720
cttggtgagg cggcgggtaa cccgaaccgt ttctgggcgt tcacttctac ttcgaagatc   780
actctcgcgg gtgcgggcgt gtccttcttc atgacttctg cggagaaccg taagtggtac   840
tccggtcatg cgggtatccg tggcattggc cctaacaagg tcaatcaagt ggctcatgcg   900
cgttactttg gcgatgctga gggagtgcgc gcggtgatgc gtaagcatgc tgcgtcgttg   960
gctccgaagt tcaacaaggt tctggagatc ctggattctc gccttgctga gtacggtgtc  1020
gcgcagtgga ctgtccctgc gggcggttac ttcatttccc ttgatgtggt tcctggtacg  1080
gcatctcgtg tggctgagtt ggctaaggaa gccggcattg cgttgacggg tgcgggttct  1140
tcttacccgc tgcgtcagga tccggagaac aagaacctcc gtttggcgcc ttctctgcct  1200
cctgttgagg aacttgaggt tgccatggat ggcgtggcta cgtgtgtttt gctggcagct  1260
gcggagcact acgctagcta g                                            1281

SEQ ID NO: 2              moltype = AA  length = 426
FEATURE                  Location/Qualifiers
source                   1..426
                         mol_type = protein
                         organism = Corynebacterium glutamicum
SEQUENCE: 2
MSSVSLQDFD AERIGLFHED IKRKFDELKS KNLKLDLTRG KPSSEQLDFA DELLALPGKG    60
DFKAADGTDV RNYGGLDGIV DIRQIWADLL GVPVEQVLAG DASSLNIMFD VISWSYIFGN   120
NDSVQPWSKE ETVKWICPVP GYDRHFSITE RFGFEMISVP MNEDGPDMDA VEELVKDPQV   180
KGMWVVPVFS NPTGFTVSED VAKRLSTMET AAPDFRVVWD NAYAVHTLTD EFPEVIDIVG   240
LGEAAGNPNR FWAFTSTSKI TLAGAGVSFF MTSAENRKWY SGHAGIRGIG PNKVNQLAHA   300
RYFGDAEGVR AVMRKHAASL APKFNKVLEI LDSRLAEYGA AQWTVPAGGY FISLDVVPGT   360
ASRVAELAKE AGIALTGAGS SYPLRQDPEN KNLRLAPSLP PVEELEVAMD GVATCVLLAA   420
AEHYAS                                                              426

SEQ ID NO: 3              moltype = DNA  length = 1179
FEATURE                  Location/Qualifiers
source                   1..1179
                         mol_type = genomic DNA
                         organism = Corynebacterium glutamicum
SEQUENCE: 3
atgaccatcg acctgcagcg ttccacccaa aacctcaccc atgaggaaat cttcgaggca    60
```

```
cacgagggcg gaaagctctc cattagttcc actcgtccgc tccgcgacat gcgcgatctt   120
tcccttgctt acaccccagg tgttgctcag gtttgtgaag caatcaaaga agatccagag   180
gttgcacgca cccacacggg cattggaaac accgtcgcgg ttatttccga cggcaccgct   240
gttcttggcc ttggcgatat cggacctcag gcatcccttc ccgtcatgga gggcaaggct   300
cagctgttca gctctttcgc tggtttgaag gctatcccta tcgtttttga tgttcacgat   360
gttgacgctt tggttgagac catcgcagcc atcgcgcctt cttcggtgc tatcaacttg    420
gaggacatct ccgctcctcg ttgcttcgag gtggagcgcc gcctcatcga gcgtctcgat   480
attccagtta tgcacgatga ccagcacggc accgctgtgg ttatcctcgc tgcgctgcgc   540
aactccctga agctgctgga tcgcaagatc gaagacctca agattgttat ttccggcgca   600
ggcgcagcgg gcgttgcagc tgtagatatg ttgaccaatg ctggcgcaac cgacatcgtt   660
gttcttgatt cccgaggcat catccacgac agccgtgagg atctttcccc agttaaggct   720
gctctcgcg agaagaccaa ccctcgtggc atcagcggtg gcatcaatga ggctttcacc     780
ggcgcggacc tgttcatcgg cgtgtccggc ggcaacatcg gcgaggacgc tctcaaactc   840
atggcaccac agccaatcct gttcaccctg gcgaacccaa ccccagagat cgatcctgaa   900
ctgtctcaga gtacggcgc catcgtcgcg accggccgct ctgacctgcc taaccagatc     960
aacaacgtgc tagcgttccc aggcatttc gccggcgctc tcgcagccaa ggccaagaag    1020
atcaccccg agatgaagct cgctgcagca gaggcaatcg ccgacatcgc agctgaggac    1080
ctcgaggtcg gccgcatcgt accgaccgcc ttggatcccc gcgtcgcccc agcagtaaag   1140
gcagctgtcc aggccgtcgc cgaagcgcaa aacgcttag                          1179

SEQ ID NO: 4          moltype = AA  length = 392
FEATURE               Location/Qualifiers
source                1..392
                      mol_type = protein
                      organism = Corynebacterium glutamicum
SEQUENCE: 4
MTIDLQRSTQ NLTHEEIFEA HEGGKLSISS TRPLRDMRDL SLAYTPGVAQ VCEAIKEDPE   60
VARTHTGIGN TVAVISDGTA VLGLGDIGPQ ASLPVMEGKA QLFSSFAGLK AIPIVLDVHD   120
VDALVETIAA IAPSFGAINL EDISAPRCFE VERRLIERLD IPVMHDDQHG TAVVILAALR   180
NSLKLLDRKI EDLKIVISGA GAAGVAAVDM LTNAGATDIV VLDSRGIIHD SREDLSPVKA   240
ALAEKTNPRG ISGGINEAFT GADLFIGVSG GNIGEDALKL MAPQPILFTL ANPTPEIDPE   300
LSQKYGAIVA TGRSDLPNQI NNVLAFPGIF AGALAAKAKK ITPEMKLAAA EAIADIAAED   360
LEVGRIVPTA LDPRVAPAVK AAVQAVAEAQ NA                                 392

SEQ ID NO: 5          moltype = DNA  length = 1740
FEATURE               Location/Qualifiers
source                1..1740
                      mol_type = genomic DNA
                      organism = Corynebacterium glutamicum
SEQUENCE: 5
atggcacaca gctacgcaga acaattaatt gacactttgg aagctcaagg tgtgaaacga   60
atttatggtt tggtgggtga cagccttaat ccgatcgtgg atgctgtccg ccaatcagat   120
attgagtggg tgcacgttag aaatgaggaa gcggcggcgt ttgcagctgg tgcggaatcg   180
ttgatcactg gggagctggc agtatgtgct gcttcttgtg gtcctggaaa cacacacctg   240
attcagggtc tttatgattc gcatcgaaat ggtgcgaagg tgttggccat cgctagccat   300
attccgagtg cccagattgg ttcgacgttc ttccaggaaa cgcatccgga gattttgttt   360
aaggaatgct ctggttactg cgagatggtg aatggtggtg agcagggtga acgcattttg   420
catcacgcga ttcagtccac catggcgggt aaaggtgtgt cggtggtagt gattcctggc   480
gatatcgcta aggaagacgc aggtgacggc acttattcca attccactat ttcctcgggc   540
actcctgtgg tgttcccgga tcctactgag gctgcagcgc tggtggaggc gattaacaac   600
gctaagtctg tcactttgtt ctgcggcgcg ggtgtgaaga atgctcgcgc gcaggtgttg   660
gagttggcgg agaagattaa atcaccaatc gggcatgcgc tgggtggtaa gcagtacatc   720
cagcatgaga tccgtttga ggtcggcatg tctggcctgc ttggttacgg cgcctgcgtg     780
gatgcgtcca tgaggcgga tctgctgatt ctgttgggta cggatttccc ttattctgat     840
ttccttccta aagataacgt tgcccaggtg gatatcaacg gtgcgcacat tggtcgacgt    900
accacggtga agtatccggt gactggtgat gttgctgcaa caatcgaaaa tatttgcct     960
catgtgaagg aaaagacaga tcgttccttc cttgatcgga tgctcaaggc acacgagcgt   1020
aagttgagct cggtggtgga gacgtacaca cataacgtcg agaagcatgt gcctattcac   1080
cctgaatacg ttgcctctat tttgaacgag ctggcggata aggacgcggt gtttaccgtg   1140
gacaccggaa tgtgcaatgt gtggcatgcg aggtacatcg aaaatccgga gggaactcgc   1200
gactttgtgg gttcattccg ccacggcacg atggctaatg cgttgcctca tgcgattggt   1260
gcgcaaagtg ccgaccggaa ccgccaggtg atcgcgatgt gtggcgatgg tggtttgggc   1320
atgctgctgg gtgagcttct gaccgttaag ctgcaccaac ttccgctgaa ggctgtggtg   1380
tttaacaaca gttctttggg catgtgaag ttggagagc tcgtggaggg acagccagaa     1440
tttggtactg accatgagga agtgaatttc gcagagattg cggcggctgc gggtatcaaa   1500
tcggtacgca tcaccgatcc gaagaaagtt cgcgagcagc tagctgaggc attggcatat   1560
cctggacctg tactgatcga tatcgtcacg gatcctaatg cgctgtcgat cccaccaacc   1620
atcacgtggg aacaggtcat gggattcagc aaggcggcca cccgaaccgt ctttggtgga   1680
ggagtaggag cgatgatcga tctggcccgt tcgaacataa ggaatattcc tactccatga   1740

SEQ ID NO: 6          moltype = AA  length = 579
FEATURE               Location/Qualifiers
source                1..579
                      mol_type = protein
                      organism = Corynebacterium glutamicum
SEQUENCE: 6
MAHSYAEQLI DTLEAQGVKR IYGLVGDSLN PIVDAVRQSD IEWVHVRNEE AAAFAAGAES   60
LITGELAVCA ASCGPGNTHL IQGLYDSHRN GAKVLAIASH IPSAQIGSTF FQETHPEILF   120
KECSGYCEMV NGGEQGERIL HHAIQSTMAG KGVSVVVIPG DIAKEDAGDG TYSNSTISSG   180
```

```
TPVVFPDPTE AAALVEAINN AKSVTLFCGA GVKNARAQVL ELAEKIKSPI GHALGGKQYI    240
QHENPFEVGM SGLLGYGACV DASNEADLLI LLGTDFPYSD FLPKDNVAQV DINGAHIGRR    300
TTVKYPVTGD VAATIENILP HVKEKTDRSF LDRMLKAHER KLSSVVETYT HNVEKHVPIH    360
PEYVASILNE LADKDAVFTV DTGMCNVWHA RYIENPEGTR DFVGSFRHGT MANALPHAIG    420
AQSADRNRQV IAMCGDGGLG MLLGELLTVK LHQLPLKAVV FNNSSLGMVK LEMLVEGQPE    480
FGTDHEEVNF AEIAAAAGIK SVRITDPKKV REQLAEALAY PGPVLIDIVT DPNALSIPPT    540
ITWEQVMGFS KAATRTVFGG GVGAMIDLAR SNIRNIPTP                          579

SEQ ID NO: 7              moltype = DNA  length = 1194
FEATURE                  Location/Qualifiers
source                   1..1194
                         mol_type = genomic DNA
                         organism = Corynebacterium glutamicum
SEQUENCE: 7
atggcattgg cacttgtttt gaactccggt tcatcttcca tcaaattcca gctggtcaac    60
cccgaaaact ctgccatcga cgagccatat gtttctggtc ttgtggagca gattggtgag   120
ccaaacggcc gcatcgtact caaagtagag ggtgaaaaat acaccctaga gacacccatc   180
gcagatcact ccgaaggcct aaacctggcg ttcgatctca tggaccagca caactggtgt   240
ccttcccaac tggaaatcac cgcagttgga caccgcgtgg tccacggtgg aatcttgttc   300
tctgcgccgg aactcatcac tgatgaaatc gttgaaatga tccgcgatct cattccactc   360
gcaccactgc acaaccctgc aaacgttgac ggcattgatg ttgctcgaaa aattctcccc   420
gatgtcccac acgtagctgt ctttgacacc ggtttcttcc actcacttcc accagcagct   480
gcactgtatg ccatcaacaa ggatgtcgca gctgaacacg gaatcaggcg ctatggtttc   540
cacggtacct cccacgaatt tgtgtccaag cgcgtggtgg aaattttgga aaagcccacc   600
gaagacatca acaccatcac cttccacctg ggcaacggcg catccatggc tgctgttcaa   660
ggcggccgtg cggtagatac ttccatgggt atgacacctc tcgcgggact tgtcatgggt   720
acccgaagcg gtgacattga tccaggtgtc gtttttccatc tctcacgcac cgctggcatg   780
agcatcgatg agatcgataa tctgctgaac aaaaagtcgg gtgtaaaggg actttccgga   840
gtcaatgatt tccgtgaact gcgggaaatg atcgacaaca atgatcaaga tgcctggtcc   900
gcgtacaaca tttacataca ccaactccgc cgctcacctcg gttcctacat ggtggcactg   960
ggacgggtag acaccatcgt gttcaccgcc ggtgttggtg aaaatgccca gtttgtccgt   1020
gaggatgcct tggcaggttt ggaaatgtac ggcatcgaaa tcgatccgga gcgcaacgca   1080
ctgccaaacta atggtcctag attgatttcc accgatgcct ccaaggtgaa ggtgtttgtt   1140
attccaacta atgaagagtt ggctatcgct aggtacgcgg tgaagttcgc ttag         1194

SEQ ID NO: 8              moltype = AA  length = 397
FEATURE                  Location/Qualifiers
source                   1..397
                         mol_type = protein
                         organism = Corynebacterium glutamicum
SEQUENCE: 8
MALALVLNSG SSSIKFQLVN PENSAIDEPY VSGLVEQIGE PNGRIVLKVE GEKYTLETPI     60
ADHSEGLNLA FDLMDQHNCG PSQLEITAVG HRVVHGGILF SAPELITDEI VEMIRDLIPL    120
APLHNPANVD GIDVARKILP DVPHVAVFDT GFFHSLPPAA ALYAINKDVA AEHGIRRYGF    180
HGTSHEFVSK RVVEILEKPT EDINTITFHL GNGASMAAVQ GGRAVDTSMG MTPLAGLVMG    240
TRSGDIDPGV VFHLSRTAGM SIDEIDNLLN KKSGVKGLSG VNDFRELREM IDNNDQDAWS    300
AYNIYIHQLR RYLGSYMVAL GRVDTIVFTA GVGENAQFVR EDALAGLEMY GIEIDPERNA    360
LPNDGPRLIS TDASKVKVFV IPTNEELAIA RYAVKFA                           397

SEQ ID NO: 9              moltype = DNA  length = 1203
FEATURE                  Location/Qualifiers
source                   1..1203
                         mol_type = genomic DNA
                         organism = Escherichia coli
SEQUENCE: 9
atgtcgagta agttagtact ggttctgaac tgcggtagtt cttcactgaa atttgccatc    60
atcgatgcag taaatggtga agagtacctt tctggtttag ccgaatgttt ccacctgccc   120
gaagcacgta tcaaatggaa aatggacggc aataaacagg aagcggcttt aggtgcaggc   180
gccgctcaca gcgaagcgct caactttatc gttaatacta ttctggcaca aaaaccagaa   240
ctgtctgcgc agctgactgc tatcggtcac cgtatcgtac acggcggcga aaagtatacc   300
agctccgtag tgatcgatga gtctgttatt cagggtatca aagatgcagc ttcttttgca   360
ccgctgcaca acccggctca cctgatcggt atcgaagaag ctctgaaatc tttcccacag   420
ctgaaagaca aaaacgttgc tgtatttgac accgcgttcc accagactat gccggaagag   480
tcttacctct acgccctgcc ttacaacctg tacaaagagc acggcatccg tcgttacggc   540
gcgcacggca ccagccactt ctatgtaacc caggaagcgg caaaaatgct gaacaaaccg   600
gtagaagaac tgaacatcat cacctgccac ctgggcaacg gtggttccgt ttctgctatc   660
cgcaacggta aatgcgttga cacctctatg ggcctgaccc cgctggaagg tctggtcatg   720
ggtacccgtt ctggtgatat cgatccggcg atcatcttcc acctgcacga caccctgggc   780
atgagccgttg acgcaatcaa caaactgctg accaaagagt ctggcctgac gggtctgacc   840
gaagtgacca gcgactgccg ctatgttgaa gacaactacg cgacgaaaga agacgcgaag   900
cgcgcaatgg acgtttactg ccaccgcctg gcgaaataca tcggtgccta cactgcgctg   960
atggatggtc gtctggacgc tgttgtattc actggtggta cggttgaaaa tgccgcaatg   1020
gttcgtgaac tgtctctggg caaactgggc gtgctgggct tgaagttga tcatgaacgc   1080
aacctggtcg cacgtttcgg caaatctggt ttcatcaaca agaaaggtac ccgtcctgcg   1140
gtggttatcc caaccaacga agaactggtt atcgcgcaag acgcgagccg cctgactgcc   1200
tga                                                              1203

SEQ ID NO: 10             moltype = AA  length = 400
FEATURE                  Location/Qualifiers
```

-continued

```
source                  1..400
                        mol_type = protein
                        organism = Escherichia coli
SEQUENCE: 10
MSSKLVLVLN CGSSSLKFAI IDAVNGEEYL SGLAECFHLP EARIKWKMDG NKQEAALGAG    60
AAHSEALNFI VNTILAQKPE LSAQLTAIGH RIVHGGEKYT SSVVIDESVI QGIKDAASFA   120
PLHNPAHLIG IEEALKSFPQ LKDKNVAVFD TAFHQTMPEE SYLYALPYNL YKEHGIRRYG   180
AHGTSHFYVT QEAAKMLNKP VEELNIITCH LGNGGSVSAI RNGKCVDTSM GLTPLEGLVM   240
GTRSGDIDPA IIFHLHDTLG MSVDAINKLL TKESGLLGLT EVTSDCRYVE DNYATKEDAK   300
RAMDVYCHRL AKYIGAYTAL MDGRLDAVVF TGGIGENAAM VRELSLGKLG VLGFEVDHER   360
NLAARFGKSG FINKEGTRPA VVIPTNEELV IAQDASRLTA                         400

SEQ ID NO: 11          moltype = DNA   length = 1008
FEATURE                Location/Qualifiers
source                 1..1008
                       mol_type = genomic DNA
                       organism = Corynebacterium glutamicum
SEQUENCE: 11
atgaacctaa agaaccccga aacgccagac cgtaaccttg ctatggagct ggtgcgagtt    60
acggaagcag ctgcactggc ttctggacgt tgggttggac gtggcatgaa gaatgaaggc   120
gacggtgccg ctgttgacgc catgcgccag ctcatcaact cagtgaccat gaagggcgtc   180
gttgttatcg gcgagggcga aaaagacgaa gctccaatgc tgtacaacgg cgaagaggtc   240
ggaaccggct ttggacctga ggttgatatc gcagttgacc cagttgacgg caccaccctg   300
atggctgagg tcgccccaa cgcaatttcc attctcgcag ctgcagagcg tggcaccatg   360
tacgatccat cctccgtctt ctacatgaag aagatcgccg tgggacctga ggccgcaggc   420
aagatcgaca tcgaagctcc agttgcccac aacatcaacg cggtggcaaa gtccaaggga   480
atcaaccctt ccgacgtcac cgttgtcgtg cttgaccgtc ctcgccacat cgaactgatc   540
gcagacattc gtcgtgcagg cgcaaaggtt cgtctcatct ccgacggcga cgttgcaggt   600
gcagttgcag cagctcagga ttccaactcc gtggacatca tgatgggcac cggcggaacc   660
ccagaaggca tcatcactgc gtgcgccatg aagtgcatgg gcggcgaaat ccagggcatc   720
ctggccccaa tgaacgattt cgagcgccag aaggcacacg acgctggtct ggttcttgat   780
caggttctgc acaccaacga tctggtgagc tccgacaact gctacttcgt ggcaaccggt   840
gtgaccaacg gtgacatgct ccgtggcgtt tcctaccgcg caaacggcgc aaccacccgt   900
tccctggtta tgcgcgcaaa gtcaggcacc atccgccaca tcgagtctgt ccaccagctg   960
tccaagctgc aggaatactc cgtggttgac tacaccaccg cgacctaa               1008

SEQ ID NO: 12          moltype = AA   length = 335
FEATURE                Location/Qualifiers
source                 1..335
                       mol_type = protein
                       organism = Corynebacterium glutamicum
SEQUENCE: 12
MNLKNPETPD RNLAMELVRV TEAAALASGR WVGRGMKNEG DGAAVDAMRQ LINSVTMKGV    60
VVIGEGEKDE APMLYNGEEV GTGFGPEVDI AVDPVDGTTL MAEGRPNAIS ILAAAERGTM   120
YDPSSVFYMK KIAVGPEAAG KIDIEAPVAH NINAVAKSKG INPSDVTVVV LDRPRHIELI   180
ADIRRAGAKV RLISDGDVAG AVAAAQDSNS VDIMMGTGGT PEGIITACAM KCMGGEIQGI   240
LAPMNDFERQ KAHDAGLVLD QVLHTNDLVS SDNCYFVATG VTNGDMLRGV SYRANGATTR   300
SLVMRAKSGT IRHIESVHQL SKLQEYSVVD YTTAT                              335

SEQ ID NO: 13          moltype = DNA   length = 1011
FEATURE                Location/Qualifiers
source                 1..1011
                       mol_type = genomic DNA
                       organism = Escherichia coli
SEQUENCE: 13
atgagacgag aacttgccat cgaatttttcc cgcgtcaccg aatcagcggc gctggctggc    60
tacaaatggt taggacgcgg cgataaaaac accgcggacg gcgcggcggt aaacgccatg   120
cgtattatgc tcaaccaggt caacattgac ggcaccatcg tcattggtga aggtgaaatc   180
gacgaagcac cgatgctcta cattggtgaa aaagtcggta ctggtcgcgg cgacgcggta   240
gatattgctg ttgatccgat tgaaggcacg cgcatgacgg cgatgggcca ggctaacgcg   300
ctggcggtgc tggcagtagg cgataaaggc tgcttcctca atgcgccgca tatgtatatg   360
gagaagctga ttgtcgggcc gggagccaaa ggcaccattg atctgaacct gccgctggcg   420
gataacctgc gcaatgtagc ggcggcgctc ggcaaaccgt tgagcgaact gacggtaacg   480
attctggcta aaccacgcca cgatgccgtt atcgctgaaa cggcgcaact ggcgtaacgg   540
gtatttgcta ttccggacgg cgacgttgcg gcctcaattc tcacctgtat gccagacagc   600
gaagttgacg tgctgtacgg tattggtggc gcgccggaag gcgtagtttc tgcggcggtg   660
atccgcgcat agatggcgga catgaacggt cgtctgctgg cgcgtcatga cgtcaaaggc   720
gacaacgaag agaatcgtcg cattggcgag caggagctgg cacgctgcaa agcgatgggc   780
atcgaagccg gtaaagtatt gcgcctgggc gatatggcag cgcgataaa cgtcatcttc   840
tctgccaccg gtattaccaa aggcgatctg ctggaaggca ttagccgcaa aggcaatatc   900
gcgactaccg aaacgctgct gatccgcggc aagtcacgca ccattcgccg cattcagtcc   960
atccactatc tggatcgcaa agacccggaa atgcaggtg acatcctctg a            1011

SEQ ID NO: 14          moltype = AA   length = 336
FEATURE                Location/Qualifiers
source                 1..336
                       mol_type = protein
                       organism = Escherichia coli
SEQUENCE: 14
```

-continued

```
MRRELAIEFS RVTESAALAG YKWLGRGDKN TADGAAVNAM RIMLNQVNID GTIVIGEGEI  60
DEAPMLYIGE KVGTGRGDAV DIAVDPIEGT RMTAMGQANA LAVLAVGDKG CFLNAPDMYM  120
EKLIVGPGAK GTIDLNLPLA DNLRNVAAAL GKPLSELTVT ILAKPRHDAV IAEMQQLGVR  180
VFAIPDGDVA ASILTCMPDS EVDVLYGIGG APEGVVSAAV IRALDGDMNG RLLARHDVKG  240
DNEENRRIGE QELARCKAMG IEAGKVLRLG DMARSDNVIF SATGITKGDL LEGISRKGNI  300
ATTETLLIRG KSRTIRRIQS IHYLDRKDPE MQVHIL                          336
```

```
SEQ ID NO: 15              moltype = DNA  length = 1602
FEATURE                    Location/Qualifiers
source                     1..1602
                           mol_type = genomic DNA
                           organism = Corynebacterium glutamicum
SEQUENCE: 15
atgattttag gcgtacccat tcaatatttg ctctattcat tgtggaattg gattgtcgat  60
accggttttg atgtagcaat tatcctggtc ttggcgtttt tgattccacg tatcggccga  120
ctggccatgc gtattatcaa gcagcgagtg gagtctgcag ccgatgcgga caccactaag  180
aaccagctcg cgttcgctgg cgttggcgtt tatatcgcgc aaattgtggc gttttttcatg  240
cttgccgtct ccgcgatgca ggcttttggt ttctctctcg cgggcgctgc gattccggca  300
accattgcgt cagctgccat tggtcttggt gcgcagtcga ttgttgcgga cttcttggcc  360
ggattttttca tcctgacgga aaagcaattc ggcgtgggtg actgggtgcg ctttgagggc  420
aacggcatcg ttgttgaagg caccgtcatt gagatcacca tgcgcgcgac caaaattcgc  480
acgattgcac aagagaccgt gatcatcccg aactccacgg cgaaagtgtg catcaacaat  540
tctaataact ggtcgcgtgc ggttgtcgtt attccgatcc ccatgttggg ttctgaaaac  600
atcacagatg tcatcgcgcg ctctgaagct gcgactcgtc gcgcacttgg ccaggagaaa  660
atcgcaccgg aaatcctcgg tgaactcgat gtgcacccag ccacggaagt cacaccgcca  720
acggtggtcg gcatgccgtg gatggtcacc atgcgtttcc tcgtgcaagt caccgccggc  780
aatcaatggc tggtcgaacg cgccatccgc acagaaatca tcaacgaatt ctgggaagaa  840
tacggcagcg caaccactac atcgggaacc ctcattgatt ccttacacgt tgagcatgaa  900
gagccaaaga cctcgcttat cgacgcctcc ccccaggctc ttaaggaacc gaagccggag  960
gctgcggcga cggttgcatc gctagctgca tcgtctaacg acgatgcaga caatgcagac  1020
gcctcggcga tcaatgcagg caatccagag aaggaacttg attccgatgt gctgaacaa  1080
gaactctcca gcgaagaacc ggaagaaaca gcaaaaccag atcactctct ccgaggcttc  1140
ttccgcactg attactaccc aaatcggtgg cagaagatcc tgtcgtttgg cggacgtgtc  1200
cgcatgagca cttccctgtt gttgggtgcg ctgctcttgc tgtcactatt taaggtcatg  1260
actgtggaac caagtgagaa ttggcaaaac tccagtggat ggctgtcacc aagcactgcc  1320
acctcaactg cggtgaccac ctccgaaact tccgcgccag caagcacgcc ttcgatgaca  1380
gtgcccacta cggtggagga gaccccaacg atggaatcta gcgtcgaaac gcagcaggaa  1440
acctcaaccc ctgcaaccgc aacgcccag cgagccgaca ccatcgaacc gaccgaggaa  1500
gccacgtcgc aggaggaaac gactgcatcg cagacgcagt ctccagcagt ggaagcacca  1560
accggtcc aagaaacagt tgcgccgacg tccaccccctt ag                    1602
```

```
SEQ ID NO: 16              moltype = AA  length = 533
FEATURE                    Location/Qualifiers
source                     1..533
                           mol_type = protein
                           organism = Corynebacterium glutamicum
SEQUENCE: 16
MILGVPIQYL LYSLWNWIVD TGFDVAIILV LAFLIPRIGR LAMRIIKQRV ESAADADTTK  60
NQLAFAGVGV YIAQIVAFFM LAVSAMQAFG FSLAGAAIPA TIASAAIGLG AQSIVADFLA  120
GFFILTEKQF GVGDWVRFEG NGIVVEGTVI EITMRATKIR TIAQETVIIP NSTAKVCINN  180
SNNWSRAVVV IPIPMLGSEN ITDVIARSEA ATRRALGQEK IAPEILGELD VHPATEVTPP  240
TVVGMPWMVT MRFLVQVTAG NQWLVERAIR TEIINEFWEE YGSATTTSGT LIDSLHVEHE  300
EPKTSLIDAS PQALKEPKPE AAATVASLAA SSNDDADNAD ASAINAGNPE KELDSDVLEQ  360
ELSSEEPEET AKPDHSLRGF FRTDYYPNRW QKILSFGGRV RMSTSLLLGA LLLLSLFKVM  420
TVEPSENWQN SSGWLSPSTA TSTAVTTSET SAPASTPSMT VPTTVEETPT MESSVETQQE  480
TSTPATATPQ RADTIEPTEE ATSQEETTAS QTQSPAVEAP TAVQETVAPT STP        533
```

```
SEQ ID NO: 17              moltype = DNA  length = 3063
FEATURE                    Location/Qualifiers
source                     1..3063
                           mol_type = genomic DNA
                           organism = Corynebacterium glutamicum
SEQUENCE: 17
atgattttag gcgtacccat tcaatatttg ctctattcat tgtggaattg gattgtcgat  60
accggttttg atgtagcaat tatcctggtc ttggcgtttt tgattccacg tatcggccga  120
ctggccatgc gtattatcaa gcagcgagtg gagtctgcag ccgatgcgga caccactaag  180
aaccagctcg cgttcgctgg cgttggcgtt tatatcgcgc aaattgtggc gttttttcatg  240
cttgccgtct ccgcgatgca ggcttttggt ttctctctcg cgggcgctgc gattccggca  300
accattgcgt cagctgccat tggtcttggt gcgcagtcga ttgttgcgga cttcttggcc  360
ggattttttca tcctgacgga aaagcaattc ggcgtgggtg actgggtgcg ctttgagggc  420
aacggcatcg ttgttgaagg caccgtcatt gagatcacca tgcgcgcgac caaaattcgc  480
acgattgcac aagagaccgt gatcatcccg aactccacgg cgaaagtgtg catcaacaat  540
tctaataact ggtcgcgtgc ggttgtcgtt attccgatcc ccatgttggg ttctgaaaac  600
atcacagatg tcatcgcgcg ctctgaagct gcgactcgtc gcgcacttgg ccaggagaaa  660
atcgcaccgg aaatcctcgg tgaactcgat gtgcacccag ccacggaagt cacaccgcca  720
acggtggtcg gcatgccgtg gatggtcacc atgcgtttcc tcgtgcaagt caccgccggc  780
aatcaatggc tggtcgaacg cgccatccgc acagaaatca tcaacgaatt ctgggaagaa  840
tacggcagcg caaccactac atcgggaacc ctcattgatt ccttacacgt tgagcatgaa  900
gagccaaaga cctcgcttat cgacgcctcc ccccaggctc ttaaggaacc gaagccggag  960
```

```
gctgcggcga cggttgcatc gctagctgca tcgtctaacg acgatgcaga caatgcagac   1020
gcctcggcga tcaatgcagg caatccagag aaggaacttg attccgatgt gctggaacaa   1080
gaactctcca gcgaagaacc ggaagaaaca gcaaaaccag atcactctct ccgaggcttc   1140
ttccgcactg attactaccc aaatcggtgg cagaagatcc tgtcgtttgg cggacgtgtc   1200
cgcatgagca cttccctgtt gttggtgcg ctgctcttgc tgtcactatt taaggggctc   1260
ttcctgtttt agagtgcatt gatcttatgt accaactgcc ctgaatggat aaggcaccgc   1320
agaatgtagt ggttcaaatt acggaaacct agagcaatcc cacgcaaatg ctccaaccgt   1380
ccgttgatcg cttcgaccgg accgttggag acaccaacat cgaaatacgc caacacatca   1440
ccaagtcgtt taaacaaact acgacccaac tgcgcgagtt ccttattcgg cccccttcaac  1500
acccgaagct gatcaataat ggtccgcatt ttcttcttcg cttcacgctt attacccatc   1560
tgataacaat caataatcgc ctgatacgca agccacgcaa gctttaacac cccgtagtct   1620
ttgtcatacg cccacaactg ctccaagctt tcttgctgac gaggactcaa ccacttgtgc   1680
gtggtcaaca aggtcttccg gtttttatac aacggatcct ggcttaaacc acgacgctgg   1740
tatttctccc gctggaggcg ttgccggcag gcggtgagct tgtcaccagc aagccgcaca   1800
acatggaatg gatccatcac gcgacgagca gaaggaatga gttctttact tgctgtggcg   1860
tagccttgga acccatccat ggacacgatc cgtatctgat tgcggaactg ttcaccgcgg   1920
gaaccaagcc aggaccgtaa agcatcagca ctacgacctg ggacgacatc taataaccgg   1980
gcaggacacc gtgagtcata ccgatgcccg gtcatatcga caatcacggt gacaaaccca   2040
tcaccatgct tagccctatt atgtgaccac ttatgctcat ccaccccaat gacatacact   2100
ccatcaagat ggtgaggatc gttatagacc agctcacggc acatatcgag ggctagttgg   2160
caggttaaat cccaccctag cccaagtgct ttcgcggttg cgtgaacact catccggtca   2220
atagcaaggc gttgcaaaat ccagcggtg acccggtggg tgacctttt accgtggtca    2280
gcgcagctta gttctgcttg gaaatacttt tgcttacatg tcgggttggt gcagcggtag   2340
cgaggtagac ggataaacag tttggtggga aacccgacga tgggtaaatc aatgagcatc   2400
cggtgggtgt gatgacgaaa caccccaggt tgggagcatt ctgggcaggt ggaggtatag   2460
tcgagtgcgt ctgcttcgat cagggtgtaa tcacctgcat cggaagcgcc ggtgatggtg   2520
agtcctagtt ccgcagtgcg gcagatggtg tcagcgatga tgttgccggt agacttcatg   2580
ggtagagcct tttgttggtg tttggttagc ttagatacct aaaccttaac cctgacaaaa   2640
ggctcgttta ttttcgggtc tacaccgcta gcccaggttc tgtgatgtac cccaaaaccg   2700
gaagggccat ttaaggtcat gactgtggaa ccaagtgaga attggcaaaa ctccagtgca   2760
tggctgtcac caagcactgc cacctcaact gcggtgacca cctccgaaac ttccgcgcca   2820
gcaagcacgc cttcgatgac agtgcccact acggtggagg agaccccaac gatggaatct   2880
agcgtcgaaa cgcagcagga aacctcaacc cctgcaaccg caacgcccca gcgagccgac   2940
accatcgaac cgaccgagga agccacgtcg caggaggaaa cgactgcatc gcagacgcag   3000
tctccagcag tggaagcacc aaccgcggtc caagaaacag ttgcgccgac gtccacccct   3060
tag                                                                 3063
```

```
SEQ ID NO: 18            moltype = AA   length = 423
FEATURE                  Location/Qualifiers
source                   1..423
                         mol_type = protein
                         organism = Corynebacterium glutamicum
SEQUENCE: 18
MILGVPIQYL LYSLWNWIVD TGFDVAIILV LAFLIPRIGR LAMRIIKQRV ESAADADTTK   60
NQLAFAGVGV YIAQIVAFFM LAVSAMQAFG FSLAGAAIPA TIASAAIGLG AQSIVADFLA   120
GFFILTEKQF GVGDWVRFEG NGIVVEGTVI EITMRATKIR TIAQETVIIP NSTAKVCINN   180
SNNWSRAVVV IPIPMLGSEN ITDVIARSEA ATRRALGQEK IAPEILGELD VHPATEVTPP   240
TVVGMPWMVT MRFLVQVTAG NQWLVERAIR TEIINEFWEE YGSATTTSGT LIDSLHVEHE   300
EPKTSLIDAS PQALKEPKPE AAATVASLAA SSNDDADNAD ASAINAGNPE KELDSDVLEQ   360
ELSSEEPEET AKPDHSLRGF FRTDYYPNRW QKILSFGGRV RMSTSLLLGA LLLLSLFKGL   420
FLF                                                                 423
```

```
SEQ ID NO: 19            moltype = DNA   length = 36
FEATURE                  Location/Qualifiers
misc_feature             1..36
                         note = primer
source                   1..36
                         mol_type = other DNA
                         organism = synthetic construct
SEQUENCE: 19
ccaagcttgc atgccatggc attggcactt gttttg                             36
```

```
SEQ ID NO: 20            moltype = DNA   length = 37
FEATURE                  Location/Qualifiers
misc_feature             1..37
                         note = primer
source                   1..37
                         mol_type = other DNA
                         organism = synthetic construct
SEQUENCE: 20
cggtacccgg ggatcctaag cgaacttcac cgcgtac                            37
```

```
SEQ ID NO: 21            moltype = DNA   length = 35
FEATURE                  Location/Qualifiers
misc_feature             1..35
                         note = primer
source                   1..35
                         mol_type = other DNA
                         organism = synthetic construct
```

-continued

```
SEQUENCE: 21
ccaagcttgc atgccatttg cgcctgcaac gtagg                              35

SEQ ID NO: 22          moltype = DNA  length = 36
FEATURE                Location/Qualifiers
misc_feature           1..36
                       note = primer
source                 1..36
                       mol_type = other DNA
                       organism = synthetic construct
SEQUENCE: 22
aagtgccaat gccataacag gaatgttcct ttcgaa                             36

SEQ ID NO: 23          moltype = DNA  length = 36
FEATURE                Location/Qualifiers
misc_feature           1..36
                       note = primer
source                 1..36
                       mol_type = other DNA
                       organism = synthetic construct
SEQUENCE: 23
aggaacattc ctgttatggc attggcactt gttttg                             36

SEQ ID NO: 24          moltype = DNA  length = 52
FEATURE                Location/Qualifiers
misc_feature           1..52
                       note = primer
source                 1..52
                       mol_type = other DNA
                       organism = synthetic construct
SEQUENCE: 24
ccaagcttgc atgcctgcag aggaggatta taatgagacg agaacttgcc at          52

SEQ ID NO: 25          moltype = DNA  length = 36
FEATURE                Location/Qualifiers
misc_feature           1..36
                       note = primer
source                 1..36
                       mol_type = other DNA
                       organism = synthetic construct
SEQUENCE: 25
cggtacccgg ggatccggac tggaaggctc aatcga                             36
```